(12) United States Patent
Touge

(10) Patent No.: US 9,382,280 B2
(45) Date of Patent: Jul. 5, 2016

(54) DIAMINE COMPOUND AND METAL COMPLEXES, AND METHOD FOR PRODUCING OPTICALLY ACTIVE COMPOUNDS

(71) Applicant: TAKASAGO INTERNATIONAL CORPORATION, Ota-ku, Tokyo (JP)

(72) Inventor: Taichiro Touge, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 50 days.

(21) Appl. No.: 14/497,732

(22) Filed: Sep. 26, 2014

(65) Prior Publication Data

US 2015/0094468 A1    Apr. 2, 2015

(30) Foreign Application Priority Data

Sep. 27, 2013 (JP) .................................. 2013-201244

(51) Int. Cl.
| | |
|---|---|
| *C07D 209/08* | (2006.01) |
| *C07D 215/06* | (2006.01) |
| *C07D 241/42* | (2006.01) |
| *C07F 15/00* | (2006.01) |
| *B01J 31/22* | (2006.01) |
| *B01J 31/18* | (2006.01) |
| *C07F 9/38* | (2006.01) |
| *C07F 17/00* | (2006.01) |

(52) U.S. Cl.
CPC ......... *C07F 15/0046* (2013.01); *B01J 31/1805* (2013.01); *B01J 31/2295* (2013.01); *C07D 209/08* (2013.01); *C07D 215/06* (2013.01); *C07D 241/42* (2013.01); *C07F 9/3808* (2013.01); *C07F 15/0033* (2013.01); *C07F 17/00* (2013.01); *B01J 2231/646* (2013.01); *B01J 2531/821* (2013.01); *B01J 2531/827* (2013.01)

(58) Field of Classification Search
CPC ................. B01J 2231/646; B01J 2531/821; B01J 2531/827; B01J 31/1805; B01J 31/2295; C07D 209/08; C07D 215/06; C07D 241/42; C07F 15/0033; C07F 15/0046; C07F 17/00; C07F 9/3808
USPC .......................................... 556/136; 564/356
See application file for complete search history.

(56) References Cited

U.S. PATENT DOCUMENTS

| 6,686,505 B2 * | 2/2004 | Watanabe et al. | 564/356 |
| 7,754,889 B2 * | 7/2010 | Amano et al. | 548/101 |

OTHER PUBLICATIONS

Grazia Zassinovich, et al., "Asymmetric Hydrogen Transfer Reactions Promoted by Homogeneous Transition Metal Catalysts", Chem. Rev., 1992, pp. 1051-1069, vol. 92.
Shonei Hashiguchi, et al., "Asymmetric Transfer Hydrogenation of Aromatic Ketones Catalyzed by Chiral Ruthenium(II) Complexes", Journal of the American Chemical Society, 1995, pp. 7562-7563, vol. 117.
Akio Fujii, et al., "Ruthenium(II)-Catalyzed Asymmetric Transfer Hydrogenation of Ketones Using a Formic Acid—Triethylamine Mixture", Journal of the American Chemical Society, 1996, pp. 2521-2522, vol. 118.
Nobuyuki Uematsu, et al., "Asymmetric Transfer Hydrogenation of Imines", Journal of the American Chemical Society, 1996, pp. 4916-4917, vol. 118.
Tianli Wang, et al., "Highly Enantioselective Hydrogenation of Quinolines Using Phosphine-Free Chiral Cationic Ruthenium Catalysts: Scope, Mechanism, and Origin of Enantioselectivity", Journal of the American Chemical Society, 2011, pp. 9878-9891, vol. 133.
Zi-Yuan Ding, et al., "Asymmetric Hydrogenation of 2,4-Disubstituted 1,5-Benzodiazepines Using Cationic Ruthenium Diamine Catalysts: An Unusual Achiral Counteranion Induced Reversal of Enantioselectivity", Angewandte Communications Int. Ed., 2012, pp. 5706-5710, vol. 51.
Takeshi Ohkuma, et al. "The Hydrogenation/Transfer Hydrogenation Network: Asymmetric Hydrogenation of Ketones with Chiral $\eta^6$-Arene/N-Tosylethylenediamine—Ruthenium(II) Catalysts", Journal of the American Chemical Society, 2006, pp. 8724-8725, vol. 128.
Karl-Josef Haack, et al., "The Catalyst Precursor, Catalyst, and Intermediate in the Ru$^{II}$-Promoted Asymmetric Hydrogen Transfer between Alcohols and Ketones", Angew. Chem. Int. Ed. Engl., 1997, pp. 285-288, vol. 36, No. 3.

* cited by examiner

*Primary Examiner* — Valerie Rodriguez-Garcia
(74) *Attorney, Agent, or Firm* — Sughrue Mion, PLLC

(57) ABSTRACT

The present invention relates to a diamine compound represented by the general formula (1), a ruthenium-diamine complex, an iridium-diamine complex, and a rhodium-diamine complex having the diamine compound as a ligand. Furthermore, the present invention relates to methods for selectively producing optically active compounds by using any of these complexes as a catalyst.

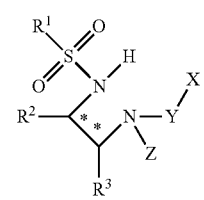

(1)

wherein $R^1$, $R^2$, $R^3$, X, Y, and Z are as defined in claim 1.

7 Claims, No Drawings

DIAMINE COMPOUND AND METAL COMPLEXES, AND METHOD FOR PRODUCING OPTICALLY ACTIVE COMPOUNDS

TECHNICAL FIELD

The present invention relates to a novel diamine compound, a ruthenium-diamine complex, an iridium-diamine complex, and a rhodium-diamine complex having the diamine compound as a ligand, and methods for selectively producing optically active compounds important as precursors for synthesis of pharmaceuticals and functional materials by using any of these complexes as a catalyst.

BACKGROUND ART

In the field of production of optically active amines, many asymmetric reactions including asymmetric reduction have been developed, and many asymmetric reactions using asymmetric metal complexes having optically active phosphine ligands have been reported. Meanwhile, there are many reports stating that complexes in which an optically active nitrogen compound is coordinated to a transition metal such as, for example, ruthenium, rhodium, or iridium have excellent performances as catalysts for asymmetric synthesis reactions (see Chem. Rev. (1992), p. 1051, J. Am. Chem. Soc. 117 (1995), p. 7562, J. Am. Chem. Soc. 118 (1996), p. 2521, and J. Am. Chem. Soc. 118 (1996), p. 4916). In particular, synthesis of optically active amines by hydrogenation reaction has been reported in recent years (see J. Am. Chem. Soc. 133 (2011), p. 9878, and Angew. Chem. Int. Ed 51 (2012), p. 5706).

However, conventional asymmetric synthesis methods using these complexes are insufficient in terms of catalytic activity or enantiomeric excess in some cases depending on the target reaction substrate. Hence, further development of such a complex has been desired.

SUMMARY OF INVENTION

An object of the present invention is to provide a metal complex having excellent catalytic activity and achieving excellent enantiomeric excess, and an asymmetric reduction catalyst comprising the complex. Another object of the present invention is to provide methods for producing an optically active amine and an optically active compound using the catalyst.

To solve the above-described problems, the present inventors have conducted intensive studies. As a result, the present inventors have found a novel optically active diamine compound, and have found that ruthenium, iridium, and rhodium complexes comprising this optically active diamine compound as a ligand have high catalytic activity and achieve excellent enantiomeric excess. These findings have led to the completion of the present invention.

Specifically, the present invention includes the following contents.

A diamine compound represented by the following general formula (1):

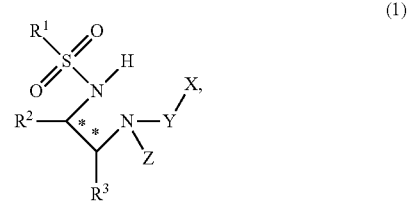

(1)

wherein
each * represents an asymmetric carbon atom,
$R^1$ represents a group selected from alkyl groups having 1 to 10 carbon atoms, halogenated alkyl groups having 1 to 10 carbon atoms, and aryl groups having 6 to 30 carbon atoms, the aryl groups optionally having one or more substituents selected from alkyl groups having 1 to 10 carbon atoms, halogenated alkyl groups having 1 to 10 carbon atoms, and halogen atoms,
$R^2$ and $R^3$ each independently represent a group selected from alkyl groups having 1 to 10 carbon atoms, phenyl groups, and cycloalkyl groups having 3 to 8 carbon atoms, the phenyl groups optionally having one or more substituents selected from alkyl groups having 1 to 10 carbon atoms, alkoxy groups having 1 to 10 carbon atoms, and halogen atoms, and each hydrogen atom of the cycloalkyl groups being optionally replaced by an alkyl group having 1 to 10 carbon atoms, or $R^2$ and $R^3$ form a ring together with carbon atoms to which $R^2$ and $R^3$ are bonded,
Y represents an alkylene group selected from optionally branched alkylene groups having 1 to 10 carbon atoms, and alkylene groups containing a benzene ring as a skeleton, the benzene ring optionally having one or more substituents selected from alkyl groups having 1 to 10 carbon atoms, alkoxy groups having 1 to 10 carbon atoms, and halogen atoms,
X represents a Brønsted acid selected from a boric acid group (—B(OH)$_2$), a carboxyl group (—COOH), a phosphoric acid group (—P(=O)(OH)$_2$), and phosphoric acid monoester groups (—P(=O)(OH)(OR$^{21}$), where $R^{21}$ represents an alkyl group having 1 to 5 carbon atoms, and
Z represents a hydrogen atom or a deuterium atom.

A ruthenium complex represented by the following general formula (2):

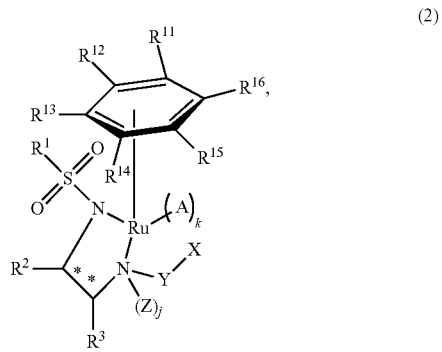

(2)

wherein each * represents an asymmetric carbon atom, $R^1$, $R^2$, $R^3$, X, Y, and Z are as defined above, $R^{11}$, $R^{12}$, $R^{13}$, $R^{14}$, $R^{15}$, and $R^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and C(=O)—OR$^{22}$, where $R^{22}$ represents an alkyl group having 1 to 10 carbon atoms, a heteroaryl group having 4 to 10 carbon atoms, or an aryl group having 6 to 10 carbon atoms, A represents a group selected from a trifluoromethanesulfonyloxy group, a p-toluenesulfonyloxy group, a methanesulfonyloxy group, a benzenesulfonyloxy group, a hydrogen atom, and halogen atoms, and j and k each represent 0 or 1, but j+k is not 1.

A ruthenium complex represented by the following general formula (3):

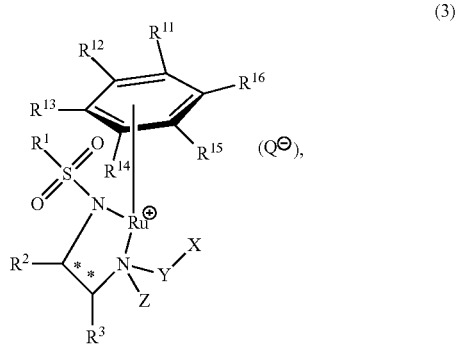

(3)

wherein each * represents an asymmetric carbon atom, $R^1$, $R^2$, $R^3$, X, Y, Z, $R^{11}$, $R^{12}$, $R^{13}$, $R^{14}$, $R^{15}$, and $R^{16}$ are as defined above, and Q⁻ represents a counter anion.

An iridium complex or rhodium complex represented by the following general formula (4):

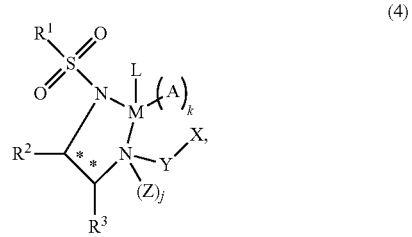

(4)

wherein each * represents an asymmetric carbon atom, $R^1$, $R^2$, $R^3$, X, Y, and Z are as defined above, A represents a group selected from a trifluoromethanesulfonyloxy group, a p-toluenesulfonyloxy group, a methanesulfonyloxy group, a benzenesulfonyloxy group, a hydrogen atom, and halogen atoms, M represents iridium or rhodium, L represents a cyclopentadienyl or pentamethylcyclopentadienyl ligand, and j and k each represent 0 or 1, but j+k is not 1.

An iridium complex or rhodium complex represented by the following general formula (5):

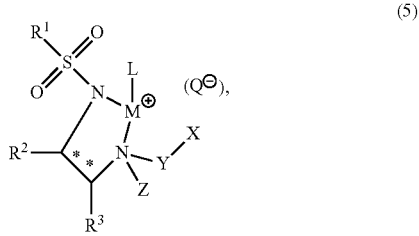

(5)

wherein each * represents an asymmetric carbon atom, $R^1$, $R^2$, $R^3$, X, Y, Z, M and L are as defined above, and Q⁻ represents a counter anion.

Moreover, the present invention also relates to methods for producing an optically active compound, the method comprising reducing an imino group of an imine compound or reducing an unsaturated bond of a heterocyclic compound in the presence of any of the above-described complexes and a hydrogen donor. Furthermore, the present invention also relates to an asymmetric reduction catalyst comprising any of the above-described complexes.

The present invention provides a diamine compound in which a nitrogen atom is substituted with a sulfonyl group, and the other nitrogen atom is substituted with an alkyl group having a Brønsted acid at its terminal. Further, the present invention provides a metal complex having the diamine compound as a ligand.

The ruthenium complex, iridium complex, and rhodium complex of the present invention exhibit higher activity or selectivity in reduction of substrates than, for example, the activity or selectivity in reduction of the same substrates with conventional complexes such as RuOTf(Tsdpen)(p-cymene) and RuBF₄(Tsdpen)(p-cymene) complexes which have been reported in J. Am. Chem. Soc., 2006, 128, p. 8724 etc. and widely used for reduction of various C=N bonds and heterocyclic compounds until now. Hence, these complexes of the present invention are useful as asymmetric reduction catalysts. Note that Tsdpen represents N-(p-toluenesulfonyl)-1,2-diphenylethylenediamine.

The use of any of the ruthenium complex, iridium complex, and rhodium complex of the present invention makes it possible to selectively produce optically active amines and optically active compounds useful as raw materials for producing pharmaceuticals and functional materials, and the like.

DESCRIPTION OF EMBODIMENTS

The present invention provides a novel optically active diamine compound represented by general formula (1), a ruthenium complex represented by general formula (2) or (3) comprising the optically active diamine compound as a ligand, and an iridium complex or rhodium complex represented by general formula (4) or (5) comprising the optically active diamine compound as a ligand. The ruthenium complex represented by general formula (2) or (3) can be synthesized by reacting the diamine compound represented by general formula (1) with a ruthenium compound. Meanwhile, the iridium complex or rhodium complex represented by general formula (4) or (5) can be synthesized by reacting the diamine compound represented by general formula (1) with an iridium compound or a rhodium compound.

The diamine compound represented by general formula (1) and the complexes represented by general formulae (2) to (5) are described in detail below.

<Optically Active Diamine Compound (Compound of Formula 1))>

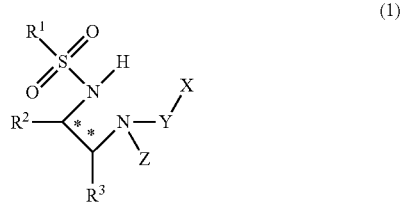
(1)

In this formula, each * represents an asymmetric carbon atom.

In formula (1), $R^1$ represents a group selected from alkyl groups having 1 to 10 carbon atoms, halogenated alkyl groups having 1 to 10 carbon atoms, and aryl groups having 6 to 30 carbon atoms, the aryl groups optionally having one or more substituents selected from alkyl groups having 1 to 10 carbon atoms, halogenated alkyl groups having 1 to 10 carbon atoms, and halogen atoms. $R^1$ in formula (1) is preferably an aryl group having 6 to 15 carbon atoms and substituted with one to three alkyl groups having 1 to 10 carbon atoms, and is more preferably a phenyl group substituted with one to three alkyl groups having 1 to 3 carbon atoms.

The alkyl group having 1 to 10 carbon atoms represented by $R^1$ of formula (1) is preferably a linear or branched alkyl group having 1 to 5 carbon atoms. Specific examples of the alkyl group having 1 to 10 carbon atoms include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like. The alkyl group is preferably a methyl group, an ethyl group, a n-propyl group, an isopropyl group, a n-butyl group, an isobutyl group, a s-butyl group, a t-butyl group, or a n-pentyl group.

The halogenated alkyl group having 1 to 10 carbon atoms represented by $R^1$ of formula (1) is the same group as the above-described alkyl group having 1 to 10 carbon atoms, except that one or multiple hydrogen atoms are replaced by one or multiple halogen atoms. The halogenated alkyl group having 1 to 10 carbon atoms is preferably a linear or branched halogenated alkyl group having 1 to 5 carbon atoms. Examples of the halogen atoms include chlorine atoms, bromine atoms, fluorine atoms, and iodine atoms. Specific examples of the halogenated alkyl groups having 1 to 10 carbon atoms include a trifluoromethane group, a trichloromethane group, a tribromomethane group, and the like.

The aryl group having 6 to 30 carbon atoms represented by $R^1$ of formula (1) may be an aromatic monocyclic group, aromatic polycyclic group, or aromatic fused cyclic group having 6 to 30 carbon atoms, and is preferably an aromatic monocyclic group, aromatic polycyclic group, or aromatic fused cyclic group having 6 to 15 carbon atoms, and particularly preferably aromatic monocyclic group having 6 to 12 carbon atoms. Specific examples of the aryl group having 6 to 30 carbon atoms include a phenyl group, a naphthyl group, an anthryl group, a phenanthryl group, an indenyl group, and the like. A phenyl group is the most preferable.

In addition, the aryl group represented by $R^1$ of formula (1) optionally has one or more substituents selected from alkyl groups having 1 to 10 carbon atoms, halogenated alkyl groups having 1 to 10 carbon atoms, and halogen atoms.

The alkyl groups and the halogenated alkyl groups as the substituents can be selected from the above-described groups defined as the alkyl groups or the halogenated alkyl groups represented by $R^1$ of formula (1). Of these groups, linear alkyl groups having 1 to 5 carbon atoms are particularly preferable.

Examples of the halogen atoms include chlorine atoms, bromine atoms, fluorine atoms, and iodine atoms.

Specific examples of the aryl group represented by $R^1$ of formula (1) and substituted with the substituents include a p-tolyl group, a 2,4,6-trimethylphenyl group, a 4-trifluoromethylphenyl group, a pentafluorophenyl group, and the like.

In formula (1), $R^2$ and $R^3$ each independently represent a group selected from alkyl groups having 1 to 10 carbon atoms, phenyl groups, and cycloalkyl groups having 3 to 8 carbon atoms, wherein the phenyl groups optionally have one or more substituents selected from alkyl groups having 1 to 10 carbon atoms, alkoxy groups having 1 to 10 carbon atoms, and halogen atoms, and each hydrogen atom of the cycloalkyl groups is optionally replaced by an alkyl group having 1 to 10 carbon atoms. Alternatively, $R^2$ and $R^3$ in formula (1) may form a ring together with carbon atoms to which $R^2$ and $R^3$ are bonded, and preferably form a cycloalkane together with the carbon atoms to which $R^2$ and $R^3$ are bonded. In formula (1), $R^2$ and $R^3$ are each independently preferably a phenyl group (provided that the phenyl group optionally has one or more substituents selected from alkyl groups having 1 to 10 carbon atoms, alkoxy groups having 1 to 10 carbon atoms, and halogen atoms).

The alkyl group having 1 to 10 carbon atoms represented by each of $R^2$ and $R^3$ of formula (1) can be selected from the groups defined as the alkyl groups having 1 to 10 carbon atoms represented by $R^1$.

In addition, the phenyl group represented by each of $R^2$ and $R^3$ of formula (1) optionally has one or more substituents selected from alkyl groups having 1 to 10 carbon atoms, alkoxy groups having 1 to 10 carbon atoms, and halogen atoms.

The alkyl groups as the substituents can be selected from the above-described groups defined as the alkyl groups represented by $R^1$ of formula (1).

Each of the alkoxy groups having 1 to 10 carbon atoms as the substituents is preferably a linear or branched alkoxy group having 1 to 5 carbon atoms. Specific examples of the alkoxy group include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group, a n-decyloxy group, and the like. The alkoxy group is preferably a methoxy group, an ethoxy group, a n-propoxy group, an isopropoxy group, a n-butoxy group, an isobutoxy group, a s-butoxy group, a t-butoxy group, or a n-pentyloxy group.

Examples of the halogen atoms as the substituents include chlorine atoms, bromine atoms, fluorine atoms, and the like.

Specific examples of the phenyl group substituted with the substituents represented by each of $R^2$ and $R^3$ of formula (1) include a 2,4,6-trimethylphenyl group, a 4-methoxyphenyl group, a 2,4,6-trimethoxyphenyl group, a 4-fluorophenyl group, a 2-chlorophenyl group, a 4-chlorophenyl group, a 2,4-dichlorophenyl group, and the like.

The cycloalkyl group having 3 to 8 carbon atoms represented by each of $R^2$ and $R^3$ of formula (1) is preferably a monocyclic, polycyclic, or bridged cycloalkyl group having 5 to 8 carbon atoms, and particularly preferably a monocyclic cycloalkyl group having 5 to 7 carbon atoms. Specific examples of the cycloalkyl group having 3 to 8 carbon atoms include a cyclopropyl group, a cyclobutyl group, a cyclopentyl group, a cyclohexyl group, a cycloheptyl group, a cyclooctyl group, and the like.

In the cycloalkyl group represented by each of $R^2$ and $R^3$ of formula (1), each hydrogen atom is optionally replaced by an alkyl group having 1 to 10 carbon atoms. Specific examples of the alkyl group as the substituent include a methyl group, an isopropyl group, a t-butyl group, and the like.

When $R^2$ and $R^3$ of formula (1) form a cycloalkane together with carbon atoms to which $R^2$ and $R^3$ are bonded, $R^2$ and $R^3$ together form an linear or branched alkylene group having 2 to 10 and preferably 3 to 10 carbon atoms, and form a preferably 4 to 8-membered and more preferably 5 to 8-membered cycloalkane ring, together with the adjacent carbon atoms. Preferred examples of the cycloalkane ring include a cyclopentane ring, a cyclohexane ring, and a cycloheptane ring. In the cycloalkane ring, each hydrogen atom is optionally replaced by an alkyl group having 1 to 10 carbon atoms. Specific examples of the alkyl group as the substituent include a methyl group, an isopropyl group, a t-butyl group, and the like.

Y in formula (1) represents an alkylene group selected from optionally branched alkylene groups having 1 to 10 carbon atoms, and alkylene groups containing a benzene ring as a skeleton, the benzene ring optionally having one or more substituents selected from alkyl groups having 1 to 10 carbon atoms, alkoxy groups having 1 to 10 carbon atoms, and halogen atoms.

The optionally branched alkylene group having 1 to 10 carbon atoms represented by Y in formula (1) may be a group obtainable by removing one hydrogen atom from any of the above-described groups defined as the alkyl groups represented by $R^1$ of formula (1), and is preferably an alkylene group having 1 to 6 carbon atoms, and particularly preferably an alkylene group having 1 to 4 carbon atoms. Specifically, the alkylene group may be a methylene group, an ethylene group, a trimethylene group, a tetramethylene group, or the like.

The alkylene group containing a benzene ring as a skeleton represented by Y in formula (1) is, for example, an alkylene group represented by the following structural formula:

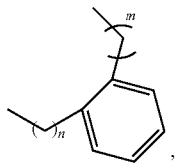

wherein n and m each independently represent an integer of 0 to 3.

In the structural formula, the benzene ring optionally has one or more substituents selected from alkyl groups having 1 to 10 carbon atoms, alkoxy groups having 1 to 10 carbon atoms, and halogen atoms, but is particularly preferably unsubstituted.

The alkyl groups as the substituents can be selected from the above-described groups defined as the alkyl groups represented by $R^1$ of formula (1).

The alkoxy groups as the substituents can be selected from the above-described groups defined as the alkoxy groups defined as the substituents of the phenyl groups represented by each of $R^2$ and $R^3$ of formula (1).

Examples of the halogen atoms as the substituents include chlorine atoms, bromine atoms, fluorine atoms, and iodine atoms.

In formula (1), X represents a Brønsted acid selected from a boric acid group (—B(OH)$_2$), a carboxyl group (—COOH), a phosphoric acid group (—P(=O)(OH)$_2$), and phosphoric acid monoester groups (—P(=O)(OH)(OR$^{21}$)), where $R^{21}$ represents an alkyl group having 1 to 5 carbon atoms. X in formula (1) is particularly preferably selected from a boric acid group and a phosphoric acid group.

$R^{21}$ in each of the phosphoric acid monoester groups represents an optionally branched alkyl group having 1 to 5 carbon atoms. Specifically, the alkyl group having 1 to 5 carbon atoms represented by $R^{21}$ may be a methyl group, an ethyl group, a n-propyl group, an isopropyl group, a n-butyl group, an isobutyl group, a s-butyl group, a t-butyl group, or a n-pentyl group, and is particularly preferably a methyl group or an ethyl group.

In formula (1), Z represents a hydrogen atom or a deuterium atom, and is preferably a hydrogen atom.

<Ruthenium Complex (Complex Represented by General Formula (2))>

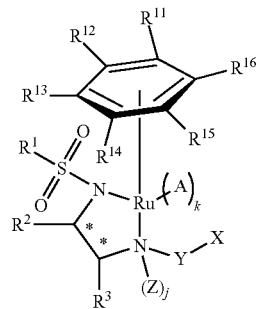

In this formula, each * represents an asymmetric carbon atom.

In formula (2), $R^1$, $R^2$, $R^3$, X, Y, and Z are as defined above.

In formula (2), $R^{11}$, $R^{12}$, $R^{13}$, $R^{14}$, $R^{15}$, and $R^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and C(=O)—OR$^{22}$, where $R^{22}$ represents an alkyl group having 1 to 10 carbon atoms, a heteroaryl group having 4 to 10 carbon atoms, or an aryl group having 6 to 10 carbon atoms. In addition, in formula (2), $R^{11}$, $R^{12}$, $R^{13}$, $R^{14}$, $R^{15}$, and $R^{16}$ are each independently selected preferably from a hydrogen atom and alkyl groups having 1 to 10 carbon atoms, further preferably from a hydrogen atom and alkyl groups having 1 to 5 carbon atoms, and particularly preferably from a hydrogen atom and alkyl groups having 1 to 3 carbon atoms.

The alkyl group having 1 to 10 carbon atoms represented by each of $R^{11}$, $R^{12}$, $R^{13}$, $R^{14}$, $R^{15}$, and $R^{16}$ in formula (2) can be selected from the groups defined as the alkyl groups having 1 to 10 carbon atoms represented by $R^1$ of formula (1), and is preferably selected from a methyl group, an ethyl group, a n-propyl group, and an isopropyl group.

The silyl group having 1 to 3 alkyl groups having 1 to 10 carbon atoms represented by each of $R^{11}$, $R^{12}$, $R^{13}$, $R^{14}$, $R^{15}$, and $R^{16}$ in formula (2) includes silyl groups substituted with 1, 2, or 3 alkyl groups, and is preferably a trialkyl-substituted silyl group. Each of the alkyl groups can be selected from the groups defined as the alkyl groups having 1 to 10 carbon atoms represented by $R^1$ of formula (1). Specifically, the alkyl group may be a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, or the like. Specific examples of the silyl groups include a trimethylsilyl group, a triethylsilyl group, a t-butyldimethylsilyl group, a triisopropylsilyl group, and the like.

The alkoxy group having 1 to 10 carbon atoms represented by each of $R^{11}$, $R^{12}$, $R^{13}$, $R^{14}$, $R^{15}$, and $R^{16}$ in formula (2) can be selected from the above-described alkoxy groups defined as the substituents of the phenyl groups represented by each of $R^2$ and $R^3$ of formula (1).

$R^{22}$ in —C(=O)—$OR^{22}$ represented by each of $R^{11}$, $R^{12}$, $R^{13}$, $R^{14}$, $R^{15}$, and $R^{16}$ in formula (2) represents an alkyl group having 1 to 10 carbon atoms, a heteroaryl group having 4 to 10 carbon atoms, or an aryl group having 6 to 10 carbon atoms. The alkyl group having 1 to 10 carbon atoms may be any one of linear, branched, and cyclic forms, and is preferably a linear alkyl group having 1 to 6 carbon atoms. The heteroaryl group having 4 to 10 carbon atoms is a heteroaryl group containing at least one hetero atom in a monocyclic, polycyclic, or fused cyclic form or the like, and is preferably a 4- to 8-membered monocyclic heteroaryl group containing 1 to 3 hetero atoms. The hetero atoms include nitrogen atoms, oxygen atoms, sulfur atoms, and the like. The aryl group having 6 to 10 carbon atoms may be in any form of an aromatic monocyclic group, an aromatic polycyclic group, and an aromatic fused cyclic group, and is preferably an aromatic monocyclic group having 6 to 8 carbon atoms. The alkyl group having 1 to 10 carbon atoms may be a methyl group, an ethyl group, a n-propyl group, a n-butyl group, a t-butyl group, a n-pentyl group, a n-hexyl group, a cyclohexyl group, or the like, and the aryl group having 6 to 10 carbon atoms may be a phenyl group or the like.

In formula (2), A represents a group selected from a trifluoromethanesulfonyloxy group, a p-toluenesulfonyloxy group, a methanesulfonyloxy group, a benzenesulfonyloxy group, a hydrogen atom, and halogen atoms, and is preferably a halogen atom. Examples of the halogen atoms include a chlorine atom, a bromine atom, an iodine atom, and the like. Of these halogen atoms, a chlorine atom is preferable.

j and k are 0 or 1, but j+k is not 1. In other words, when k is 1, j is also 1, or when k is 0, j is also 0.

<Ruthenium Complex (Complex Represented by General Formula (3))>

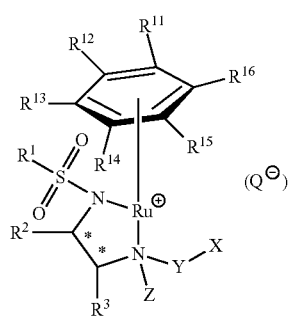

(3)

In this formula, each * represents an asymmetric carbon atom.

In formula (3), $R^1$, $R^2$, $R^3$, X, Y, Z, $R^{11}$, $R^{12}$, $R^{13}$, $R^{14}$, $R^{15}$, and $R^{16}$ are as defined above.

In formula (3), $Q^-$ represents a counter anion. Specifically, the counter anion may be an ion such as $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, or $B(3,5-(CF_3)_2C_6F_3)_4^-$. Of these ions, $BF_4^-$ is preferable.

<Iridium or Rhodium Complex (Complex Represented by General Formula (4))>

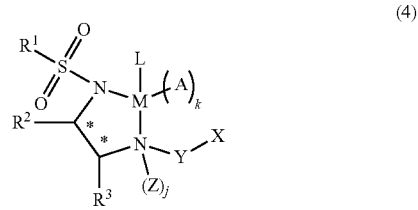

(4)

In this formula, each * represents an asymmetric carbon atom.

In formula (4), $R^1$, $R^2$, $R^3$, X, Y, Z, and A are as defined above.

In formula (4), M represents iridium or rhodium.

In formula (4), L represents a Cp (cyclopentadienyl) or Cp*(pentamethylcyclopentadienyl) ligand.

In formula (4), j and k each represent 0 or 1, but j+k is not 1.

<Iridium or Rhodium Complex (Complex Represented by General Formula (5))>

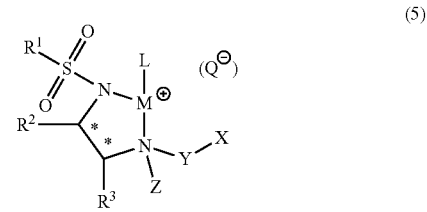

(5)

In this formula, each * represents an asymmetric carbon atom.

In formula (5), $R^1$, $R^2$, $R^3$, X, Y, Z, M, L, and $Q^-$ are as defined above.

<Methods for Producing Diamine Compounds of General Formula (1)>

The diamine compound represented by general formula (1) of the present invention can be produced, for example, by a method described in any one of the following schemes 1 to 4.

Note that *, $R^1$, $R^2$ and $R^3$ in the following schemes 1 to 4 are as defined above.

(Scheme 1)

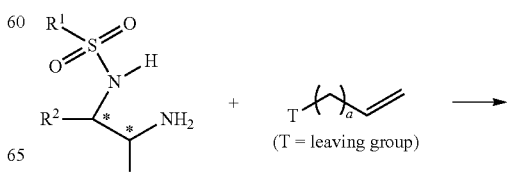

(T = leaving group)

-continued

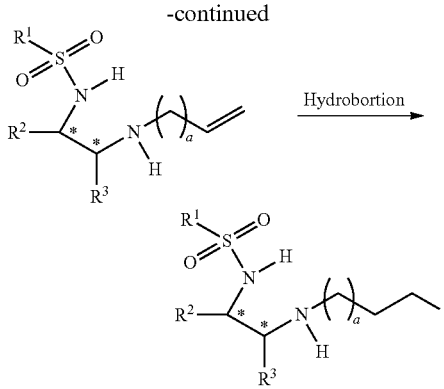

In scheme 1, a is an integer of 1 to 3.

A diamine is reacted with a compound having a terminal alkene to obtain a diamine having a side chain containing the terminal alkene. Then, hydroboration of the alkene moiety is carried out. Thus, a diamine compound having boric acid on a terminal side chain can be obtained.

(Scheme 2)

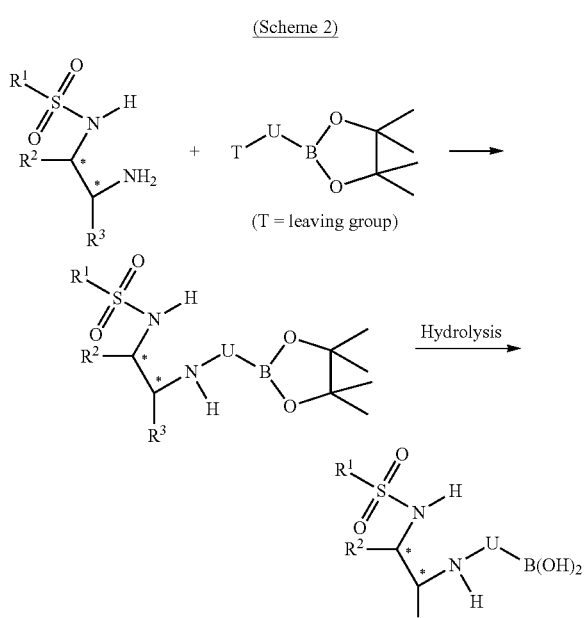

In scheme 2, U represents

wherein a represents an integer of 1 to 3, or

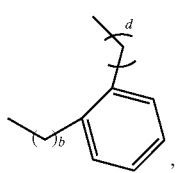

wherein b and d each represent an integer of 0 to 3.

A diamine is reacted with a compound having a boron atom protected with pinacol or the like and having a leaving group to obtain a diamine compound having the boron atom on a terminal side chain. Then, hydrolysis with an acid or the like is carried out. Thus, a diamine compound having boric acid on a terminal side chain can be obtained.

(Scheme 3)

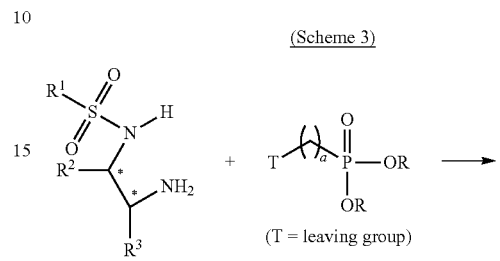

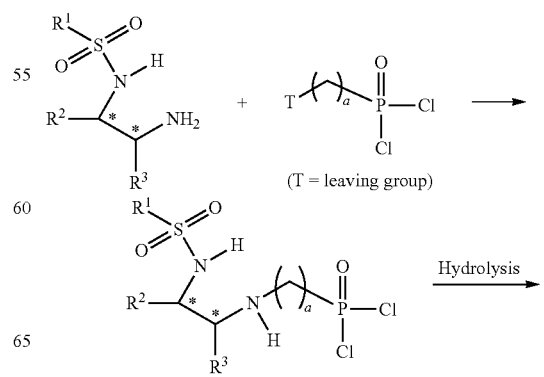

In scheme 3, R is an alkyl group having 1 to 5 carbon atoms.

In scheme 3, a is an integer of 1 to 3.

A diamine is reacted with a phosphate ester having a leaving group or the like to obtain a diamine compound having a phosphate ester at its terminal. Then, hydrolysis with an acid or the like is carried out. Thus, a diamine compound having a phosphoric acid on a terminal side chain can be obtained.

(Scheme 4)

-continued

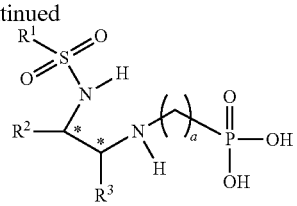

5

-continued

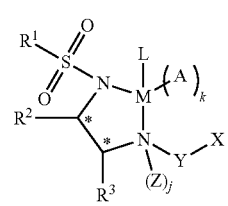

(4)

In scheme 4, a is an integer of 1 to 3.

A diamine is reacted with a phosphoric acid dichloride having a leaving group or the like to obtain a diamine compound having phosphoric acid dichloride at its terminal. Then, hydrolysis with water or the like is carried out. Thus, a diamine compound having a phosphoric acid on a terminal side chain can be obtained.

<Methods for Producing Complexes of General Formula (2) and General Formula (4)>

The ruthenium complex represented by general formula (2) and the rhodium or iridium complex represented by general formula (4) of the present invention can be produced by, for example, the method shown in the following scheme 5 or 6 described in J. Am. Chem. Soc. 117 (1995), p. 7562 or Angew. Chem. Int. Ed. Engl., 1997, 36, p. 285.

Note that *, $R^1$, $R^2$, $R^3$, X, Y, Z, A, $R^{11}$, $R^{12}$, $R^{13}$, $R^{14}$, $R^{15}$, $R^{16}$, M, L, j and k in the following schemes 5 and 6 are as defined above.

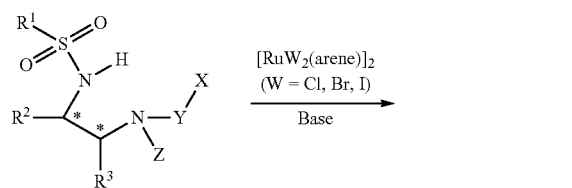

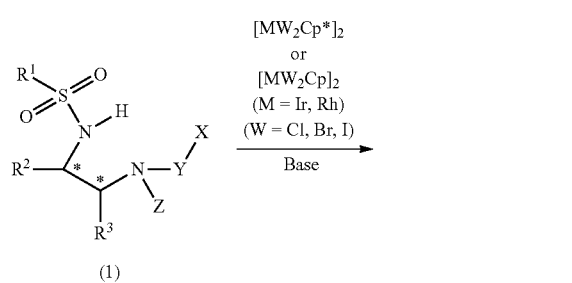

Here, solvents used in schemes 5 to 6 include, but are not particularly limited to, ethers such as diethyl ether and tetrahydrofuran; alcohols such as methanol, ethanol, and isopropanol; aromatic hydrocarbons such as toluene and xylene; aprotic polar solvents such as acetonitrile and N,N-dimethylformamide; halogen-containing solvents such as dichloromethane and chloroform; and the like. Of these solvents, isopropanol and dichloromethane are preferable.

The reaction between the diamine compound represented by general formula (1) and the ruthenium compound in scheme 5 is theoretically an equimolar reaction, but it is preferable to use the diamine compound in an equimolar amount or more to the ruthenium compound from the viewpoint of the catalyst preparation rate.

The reaction between the diamine compound represented by general formula (1) and the iridium compound or the rhodium compound in scheme 6 is theoretically an equimolar reaction, but it is preferable to use the diamine compound in an equimolar amount or more to the iridium or rhodium compound from the viewpoint of the catalyst preparation rate.

In addition, when the ruthenium complex of general formula (2) or the iridium or rhodium complex of general formula (4) in which A is a halogen atom is prepared, it is preferable to conduct the reaction in the coexistence of a base. In this case, the base may be a tertiary organic amine such as trimethylamine, triethylamine, triisopropylamine, or diisopropylethylamine; an inorganic base such as LiOH, NaOH, KOH, or $K_2CO_3$; or a metal alkoxide such as sodium methoxide or potassium methoxide. Of these bases, tertiary organic amines are preferable, and triethylamine is particularly preferable. The amount of the base added is preferably equimolar or more to the ruthenium atoms, the iridium atoms, or the rhodium atoms.

Examples of the ruthenium compound serving as a starting material of the ruthenium complex represented by general formula (2) include [RuCl$_2$(p-cymene)]$_2$, [RuI$_2$(p-cymene)]$_2$, [RuBr$_2$(p-cymene)]$_2$, [RuBr$_2$(benzene)]$_2$, [RuBr$_2$(benzene)]$_2$, [RuCl$_2$(benzene)]$_2$, [RuBr$_2$(mesitylene)]$_2$, [RuI$_2$(mesitylene)]$_2$, [RuCl$_2$(mesitylene)]$_2$, [RuCl$_2$(hexamethylbenzene)]$_2$, [RuI$_2$ (hexamethylbenzene)]$_2$, [RuBr$_2$ (hexamethylbenzene)]$_2$, [RuBr$_2$(toluene)]$_2$, [RuI$_2$ (toluene)]$_2$, [RuCl$_2$ (toluene)]$_2$, [RuBr$_2$(xylene)]$_2$, [RuI$_2$(xylene)]$_2$, [RuCl$_2$ (xylene)]$_2$, [RuCl$_2$(TMS-benzene)]$_2$, [RuCl$_2$ (TMS-toluene)]$_2$, and the like.

Note that cod represents 1,5-cyclooctadiene, and TMS represents trimethylsilyl.

Examples of the iridium compound or the rhodium compound serving as a starting material of the iridium complex or rhodium complex represented by general formula (4) include [IrCp*Cl$_2$]$_2$, [IrCpCl$_2$]$_2$, [RhCp*Cl$_2$]$_2$, [RhCpCl$_2$]$_2$, [IrCp*Br$_2$]$_2$, [IrCpBr$_2$]$_2$, [RhCp*Br$_2$]$_2$, [RhCpBr$_2$]$_2$, [IrCp*I$_2$]$_2$, [IrCpI$_2$]$_2$, [RhCP*I$_2$]$_2$, [RhCpI$_2$]$_2$, and the like.

<Methods for Producing Complexes of General Formula (3) and General Formula (5)>

The cationic ruthenium complex represented by general formula (3) can be obtained by reacting a ruthenium complex represented by general formula (2) in which A is a halogen atom or the like with a metal salt represented by G-Q.

The cationic iridium or rhodium complex represented by general formula (5) can be obtained by reacting an iridium or rhodium complex represented by general formula (4) in which A is a halogen atom or the like with a metal salt represented by G-Q.

The production methods are shown in schemes 7 and 8.

Note that, in the following schemes 7 and 8, *, $R^1$, $R^2$, $R^3$, X, Y, Z, A, $Q^-$, $R^{11}$, $R^{12}$, $R^{11}$, $R^{14}$, $R^{15}$, $R^{16}$, M, M, L, j, and k are as defined above.

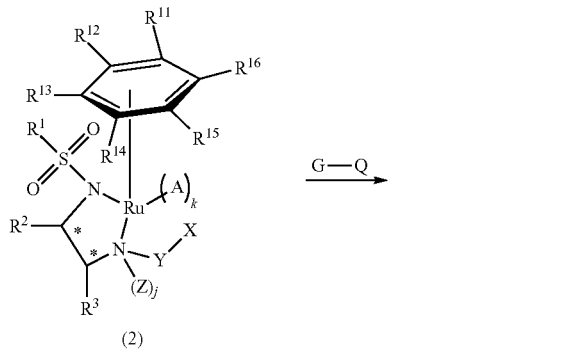

(Scheme 7)

(2)

(3)

(Scheme 8)

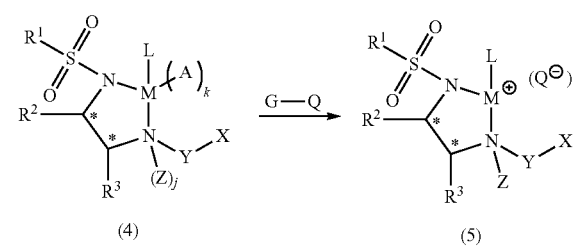

(4)

(5)

Examples of the metal G in G-Q in each of schemes 7 and 8 include silver (Ag), sodium (Na), potassium (K), lithium (Li), and the like. Examples of Q include alkanesulfonyloxys and arenesulfonyloxys such as trifluoromethanesulfonyloxy (TfO), p-toluenesulfonyloxy (TsO), methanesulfonyloxy (MsO), and benzenesulfonyloxy (BsO), and further include $BF_4$, $SbF_6$, $CF_3COO$, $CH_3COO$, $PF_6$, $NO_3$, $ClO_4$, SCN, OCN, $ReO_4$, $MoO_4$, $BPh_4$, $B(C_6F_5)_4$, $B(3,5-(CF_3)_2C_6F_3)_4$, and the like.

Examples of the metal salt represented by G-Q include AgOTf, AgOTs, AgOMs, AgOBs, $AgBF_4$, $AgSbF_6$, $CF_3COOAg$, $CH_3COOAg$, $AgPF_6$, $AgNO_3$, $AgClO_4$, AgSCN, AgOCN, $AgReO_4$, $AgMoO_4$, NaOTf, $NaBF_4$, $NaSbF_6$, $CF_3COONa$, $CH_3COONa$, $NaPF_6$, $NaNO_3$, $NaClO_4$, NaSCN, KOTf, $KBF_4$, $KSbF_6$, $CF_3COOK$, $CH_3COOK$, $KPF_6$, $KNO_3$, $KClO_4$, KSCN, $KBPh_4$, $KB(C_6F_5)_4$, $KB(3,5-(CF_3)_2C_6F_3)_4$, LiOTf, $LiBF_4$, $LiSbF_6$, $CF_3COOLi$, $CH_3COOLi$, $LiPF_6$, $LiNO_3$, $LiClO_4$, LiSCN, $LiBPh_4$, $LiB(C_6F_5)_4$, $LiB(3,5-(CF_3)_2C_6F_3)_4$, and the like.

The amount of the metal salt G-Q used in each of schemes 7 and 8 is equimolar or more to the ruthenium atoms, the iridium atoms, or the rhodium atoms.

In addition, solvents used in schemes 7 and 8 include, but are not particularly limited to, alcohols such as methanol, ethanol, and isopropanol; aromatic hydrocarbons such as toluene and xylene; halogenated hydrocarbons such as dichloromethane and 1,2-dichloroethane; aprotic polar solvents such as acetonitrile and N,N-dimethylformamide; ethers such as diethyl ether, and tetrahydrofuran; and the like. Of these solvents, methanol and dichloromethane are preferable. One of these solvents may be used alone, or a mixture of multiple solvents may be used.

After completion of the reaction for preparing the complex, the desired ruthenium complex, iridium complex, or rhodium complex can be separated by a common crystallization technique such as concentration of the reaction liquid or addition of a poor solvent.

In addition, when a hydrogen halide salt is by-produced in the preparation of the above-described complex, a washing operation with water may be conducted, if necessary.

The thus obtained complexes represented by general formulae (2), (3), (4), and (5) of the present invention can be used as asymmetric reduction catalysts.

An asymmetric reduction reaction may be conducted by using, as a catalyst, an isolated one of the ruthenium complex represented by general formula (2) or (3) or the iridium complex or rhodium complex represented by general formula (4) or (5) of the present invention. Alternatively, the reaction may be conducted by using the reaction liquid for preparation of the complex as it is without isolation of the complex (an in situ method).

By bringing the ruthenium complex represented by general formula (2) or the iridium complex or rhodium complex represented by general formula (4) in which A is other than a hydrogen atom into contact with a hydrogen donor, the complex can be easily converted to a complex represented by the general formula in which A is a hydrogen atom.

Here, as the hydrogen donor, those generally used as a hydrogen donor in a hydrogen transfer reduction reaction, such as hydrogen gas, metal hydrides including borohydride compounds, formic acid, salts thereof, and isopropanol, can be used. The amount of the hydrogen donor used only needs to be equimolar or more to the complex of general formula (2) or general formula (4) in terms of hydride.

In addition, the conversion of A in the complex of the present invention to a hydrogen atom may be conducted in advance prior to the use for an asymmetric reduction reaction or may be conducted in an asymmetric reduction reaction system.

<Asymmetric Reduction Reactions>

Asymmetric reduction reactions of the present invention include (i) a reaction in which the complex represented by any of general formulae (2) to (5) is used as a catalyst, and an optically active amine is produced by reducing an imino group of an imine compound in the coexistence of a hydrogen donor, or (ii) a reaction in which the complex represented by any of general formulae (2) to (5) is use as a catalyst, and an optically active compound is produced by reducing an unsaturated bond of a heterocyclic compound in the coexistence of a hydrogen donor.

The hydrogen donor is not particularly limited, as long as the hydrogen donor is a hydrogen donor generally used for a hydrogen transfer reduction reaction, such as hydrogen gas, formic acid, an alkali metal formate, or an alcohol having a hydrogen atom on a carbon atom at an α-position of a carbon atom substituted with a hydroxyl group. The alcohol may be isopropanol or the like. Examples of the alkali metal formate include sodium formate, potassium formate, lithium formate, and the like.

In the asymmetric reduction reaction, a base may be used. The base may be a tertiary organic amine such as trimethylamine, triethylamine, or triisopropylamine; an inorganic base such as LiOH, NaOH, KOH, or $K_2CO_3$; or a metal alkoxide such as sodium methoxide or potassium methoxide.

When the hydrogen donor is formic acid, an amine is preferably used as the base. In this case, formic acid and the amine may be added to the reaction system separately, or a mixture of formic acid and the amine prepared in advance may be used. A preferred mixture of formic acid and an amine is an azeotrope or the like.

For a reaction using hydrogen gas as the hydrogen donor, an alcohol such as methanol, ethanol, 2-propanol, tert-butyl alcohol, trifluoroethanol, or hexafluoroisopropanol, an aprotic solvent such as toluene, tetrahydrofuran, 2-methyltetrahydrofuran, acetonitrile, or acetone, a halogen-containing solvent such as dichloromethane or chloroform, or the like is used as the reaction solvent.

For a reaction using formic acid or an alkali metal formate as the hydrogen donor, in general, the hydrogen donor itself can be used as the reaction solvent, when the hydrogen donor is a liquid. It is also possible to use, as an auxiliary solvent, one or a mixture of non-hydrogen-donating solvents such as toluene, tetrahydrofuran, acetonitrile, dimethylformamide, dimethyl sulfoxide, acetone, and methylene chloride, in order to dissolve the raw material. When an alkali metal formate is used, it is also possible to conduct the reaction in a two-layer system in which water is used as an auxiliary solvent in combination with an organic solvent, to dissolve the alkali metal formate. In this case, it is also possible to use a phase-transfer catalyst in combination, to accelerate the reaction.

The amount of the complex represented by any of general formulae (2) to (5) used as the catalyst is selected such that the molar ratio (S/C) of a substrate (S) (i.e., an imine compound or a heterocyclic compound) to ruthenium, iridium, or rhodium metal atoms (C) can be in a range from 10 to 1000000, and preferably from 50 to 15000.

The amount of the hydrogen donor relative to the imine compound or the heterocyclic compound is generally equimolar or more, and the amount in moles of the hydrogen donor used is in a range of 20 times or less, and preferably 10 times or less of the imine compound or the heterocyclic compound. Of these hydrogen donors, when the hydrogen donor is formic acid or an alkali metal formate, the amount in moles of the hydrogen donor is preferably 1.5 times or more, and the amount in moles of the hydrogen donor used is in a range from 20 times or less, and preferably 10 times or less.

Meanwhile, when the hydrogen donor is isopropanol or the like, the hydrogen donor is used in a large excess relative to the substrate from the viewpoint of the reaction equilibrium, and the amount in moles of the hydrogen donor used is generally in a range of 1000 times or less of the amount in moles of the substrate.

The reaction temperature is selected in a range from −20 to 100° C. and preferably from 0 to 70° C.

The reaction pressure is not particularly limited, and the reaction is conducted generally at 0.5 to 2 atm, and preferably at atmospheric pressure.

In addition, when hydrogen gas is used, the pressure is generally 5 MPa or lower.

The reaction time varies depending on the catalyst ratio, but is 1 to 100 hours, and generally 2 to 50 hours.

After the reaction, the formed optically active compound can be separated and purified by a common operation such as distillation, extraction, chromatography, or recrystallization.

Hereafter, the present invention will be described in more detail with reference to the following Examples, which do not limit the present invention.

EXAMPLES

In the following Examples and the like, NMR spectra used for identification and purity determination of complexes were measured with a Mercury Plus 300 4N model apparatus manufactured by Varian Technologies Japan, Ltd. or Bruker BioSpin Avance III 500 System. For GC analyses, Chirasil-DEX CB (0.25 mm×25 m, 0.25 µm) (manufactured by Varian, Inc.) or HP-1 (0.32 mm×30 m, 0.25 µm) (manufactured by Agilent Technologies, Inc.) was used. For HPLC analyses, YMC-Pack Pro C18 (250×4.6 mm, 5 µm, 12 nm) (manufactured by YMC CO., LTD.) was used. Meanwhile, for the MS measurement, JMS-T 100GCV manufactured by JEOL Ltd. or LCMS-IT-TOF manufactured by Shimadzu Corporation was used.

In addition, abbreviations in Examples have the following meanings.

DIPEA: Diisopropylethylamine

HFIP: Hexafluoroisopropanol $^i$Pr: Isopropyl n-Bu: n-Butyl

Ts: Tosyl

Ph: Phenyl

EtOAc: Ethyl acetate

Me: Methyl

B(Pin): Pinacolborane group

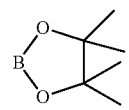

p-cymene: p-Isopropyltoluene

Example 1

Synthesis of 2-(Bromomethyl)-4,4,5,5-tetramethyl-1,3,2-dioxaborolane (Raw Material for Synthesizing Diamine Compound of Formula (1))

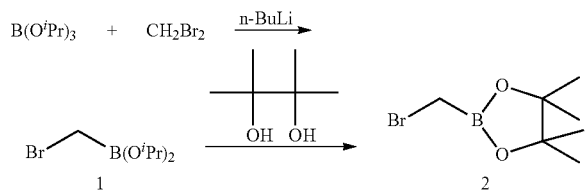

To a 500 mL 4-necked reaction flask, a three-way stopcock, a stirrer bar, a dropping funnel, and a thermometer were attached, and the inside of the flask was purged with nitrogen. To this reaction flask, 24.8 g (131.8 mmol) of B(O$^i$Pr)$_3$, 25 g (10.1 mL, 143.8 mmol) of CH$_2$Br$_2$, and 186 mL of tetrahydrofuran (hereinafter referred to as THF) were introduced under nitrogen stream, followed by cooling to −78° C. In the dropping funnel, 77.8 mL (119.8 mmol) of n-BuLi (1.59 M hexane solution) was introduced, and added dropwise over 20 minutes. After the temperature was raised to room temperature, the mixture was stirred for 2 hours. This mixture was cooled with an ice bath to 0° C., and 11.5 g (119.8 mmol) of methanesulfonic acid was added thereto. Then, the mixture was stirred again at room temperature for 1 hour. The mixture was again cooled to 0° C., and 14.2 g (119.8 mmol) of pinacol was added. Then, the mixture was stirred at room temperature for 1 hour. The solvent was removed from the mixture with an evaporator, and then distillation was conducted under reduced pressure. Thus, 18.6 g of compound 2 was obtained (yield: 70.3%).

$^1$H-NMR (CDCl$_3$, 300 MHz): δ 2.58 (s, 2H), 1.28 (s, 12H).

Example 2

Synthesis of ((1S,2S)-2-(4-Methylphenylsulfonamido)-1,2-diphenylethylamino)methylboronic acid (Diamine Compound of Formula (1))

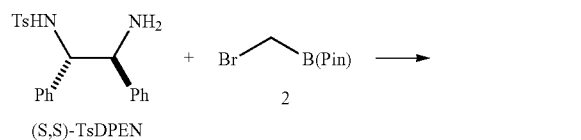

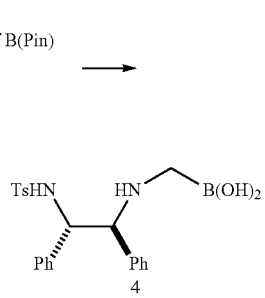

In 20 mL of toluene, 4.0 g (10.9 mmol) of (S,S)-TsDPEN, 2.41 g (10.9 mmol) of compound 2 obtained in Example 1, and 1.41 g (1.9 mL, 10.9 mmol) of DIPEA were dissolved, and a reaction was conducted in an oil bath of 130° C. under reflux for 10 hours. The precipitated salt was removed by a filtration, and then 40 mL of a 2 M aqueous HCl solution was added to this reaction liquid. The reaction was further conducted at 60° C. for 1 hour. Toluene was removed from the reaction liquid with an evaporator, and then 15 mL of methanol was added. Further, the pH was adjusted to approximately 8 by adding an aqueous NaHCO$_3$ solution. Then, all the solvent was removed from the reaction liquid, followed by purification by silica gel column chromatography (EtOAc 100%→MeOH 100%). Thus, 1.39 g of compound 4, which was a diamine compound of formula (1) according to the present invention, was obtained (yield: 30.0%).

$^1$H-NMR (CD$_3$OD, 300 MHz): δ 7.30 (d, 2H), 7.22-6.80 (m, 12H), 5.25 (d, 1H), 5.12 (d, 1H), 2.60 (d, 1H), 2.22 (s, 3H), 2.00 (d, 1H).

Example 3

Synthesis of Ruthenium Complex ((S,S)—BL-N-09-Cl) (Ruthenium Complex of Formula (2))

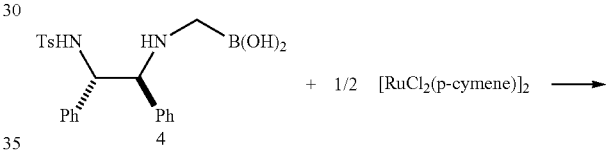

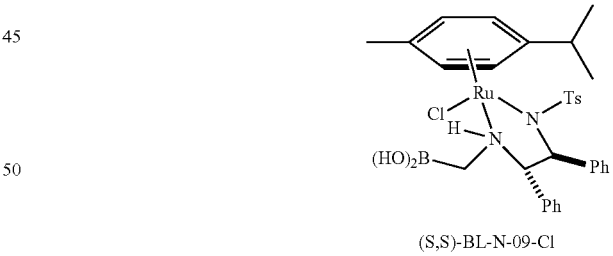

In 10 mL of 2-propanol, 0.3 g (0.707 mmol) of diamine compound 4 obtained in Example 2, 0.216 g (0.35 mmol) of [RuCl$_2$(p-cymene)]$_2$, and 0.215 g (0.30 mL, 2.12 mmol) of triethylamine were dissolved, and a reaction was conducted at 75° C. for 1 hour. After that, the solvent was recovered from the reaction liquid, and 10 mL of water was added, followed by stirring under ice-cooling for 10 minutes. The precipitated crystals were filtered, and then dried under reduced pressure. Thus, 0.35 g of (S,S)—BL-N-09-Cl, which was a ruthenium complex of the present invention, was obtained (yield: 71.4%).

HRMS (ESI) calcd for $C_{32}H_{38}BN_2O_4RuS$ $[M-Cl]^+$ 659.1689. found 659.1672.

Example 4

Synthesis of Ruthenium Complex ((S,S)—BL-N-09-BF$_4$) (Ruthenium Complex of Formula (3))

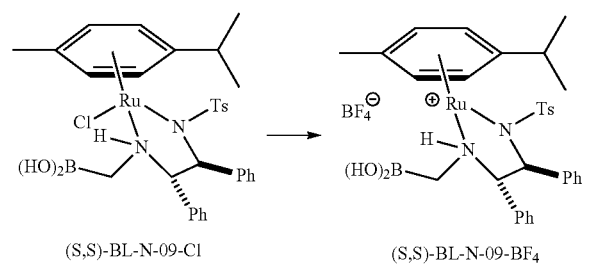

(S,S)-BL-N-09-Cl    (S,S)-BL-N-09-BF$_4$

In 15 mL of methanol, 0.35 g (0.504 mmol) of the ruthenium complex (S,S)—BL-N-09-Cl obtained in Example 3 and 0.118 g (0.605 mmol) of AgBF$_4$ were stirred for 1 hour, and the precipitated salt was filtered through Celite. Then, the filtrate was concentrated with an evaporator, and dried under reduced pressure. Thus, 0.37 g of (S,S)—BL-N-09-BF$_4$, which was a ruthenium complex of the present invention, was obtained (yield: 98%).

HRMS (ESI) calcd for $C_{32}H_{38}BN_2O_4RuS$ $[M-BF_4]^+$ 659.1689. found 659.1622.

Example 5

Synthesis of N-((1R,2R)-2-(But-3-enylamino)-1,2-diphenylethyl)-4-methylbenzenesulfonamide (Raw Material for Synthesizing Diamine Compound of Formula (1))

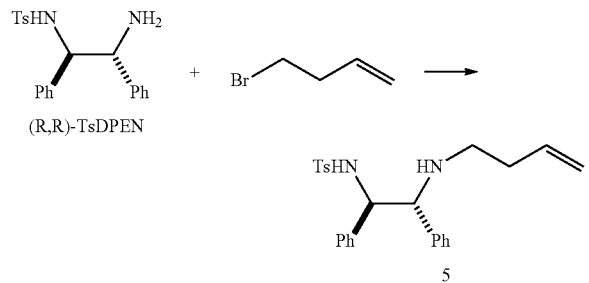

In 50 mL of toluene, 11.26 g (30.72 mmol) of (R,R)-TsDPEN, 4.15 g (3.1 mL, 30.72 mmol) of 4-bromo-1-butene, and 3.97 g (5.35 mL, 30.72 mmol) of DIPEA were dissolved, and a reaction was conducted in an oil bath of 130° C. under reflux for 17 hours. The reaction liquid was cooled with ice, and the precipitated salt was filtered. Then, the solvent was removed with an evaporator, and the concentrate was purified by silica gel column chromatography (EtOAc/hexane=5/1 (volume ratio)→3/1). Thus, 11.95 g of compound 5 was obtained (yield: 92.4%).

$^1$H-NMR (CDCl$_3$, 300 MHz): δ 7.41-7.39 (d, 2H), 7.18-6.90 (m, 12H), 5.65-5.55 (m, 1H), 5.05-4.93 (m, 2H), 4.25 (d, 1H), 3.65 (d, 1H), 2.50-2.35 (m, 2H), 2.35 (s, 3H), 2.20-2.10 (m, 2H).

Example 6

Synthesis of 4-((1R,2R)-2-(4-Methylphenylsulfonamido)-1,2-diphenylethylamino)butylboronic Acid (Diamine Compound of Formula (1))

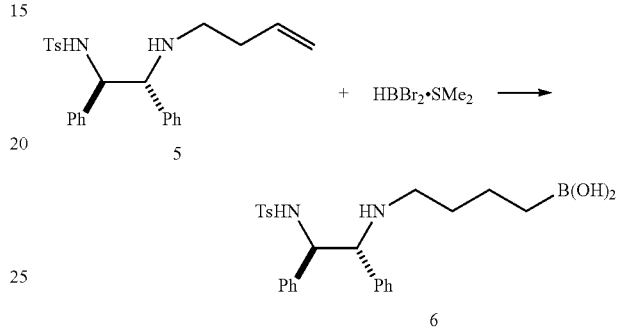

In 50 mL of dichloromethane, 5.0 g (11.9 mmol) of compound 5 obtained in Example 5 was dissolved, and 23.8 mL (23.8 mmol) of HBBr$_2$.SMe$_2$ (1.0 M ether solution) was added thereto. Then, a reaction was conducted at 50° C. for 16 hours. The reaction liquid was cooled to normal temperature, and 50 mL of water and 50 mL of diethyl ether were added thereto, followed by stirring at room temperature for 20 minutes. All the solvent was removed from the reaction liquid with an evaporator, and the concentrate was purified by silica gel column chromatography (EtOAc 100%→EtOAc/MeOH=2/1 (volume ratio)). Thus, 4.32 g of compound 6, which was a diamine compound of formula (1) according to the present invention, was obtained (yield: 78.0%).

$^1$H-NMR (CD$_3$OD, 300 MHz): δ 7.48-7.42 (d, 2H), 7.25-7.22 (m, 5H), 7.05-7.00 (d, 2H), 6.90-6.70 (m, 5H), 4.73 (d, 1H), 4.60 (d, 1H), 3.62-3.58 (m, 1H), 2.95-2.78 (m, 2H), 1.90-1.60 (m, 2H), 1.42-1.30 (m, 2H), 1.25-1.18 (m, 2H), 0.83-0.78 (m, 2H).

Example 7

Synthesis of Ruthenium Complex ((R,R)—BL-N-06-Cl) (Ruthenium Complex of Formula (2))

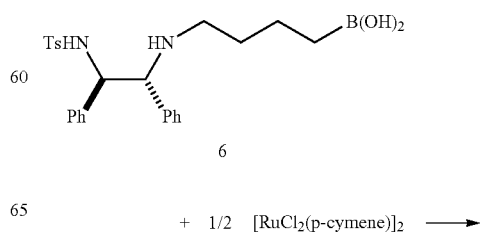

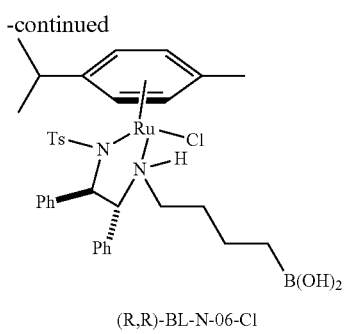

(R,R)-BL-N-06-Cl

In 15 mL of 2-propanol, 0.5 g (1.072 mmol) of diamine compound 6 obtained in Example 6, 0.328 g (0.536 mmol) of [RuCl$_2$(p-cymene)]$_2$, and 0.3254 g (0.448 mL, 3.22 mmol) of triethylamine were dissolved, and a reaction was conducted at 80° C. for 1 hour. After that, the solvent was recovered from the reaction liquid, and 20 mL of water was added, followed by stirring under ice-cooling for 10 minutes. The precipitated crystals were filtered, and then dried under reduced pressure. Thus, 0.67 g of (R,R)—BL-N-06-Cl, which was a ruthenium complex of the present invention, was obtained (yield: 84.9%).

HRMS (ESI) calcd for C$_{35}$H$_{44}$BN$_2$O$_4$RuS [M-Cl]$^+$ 701.2158. found 701.2144.

Example 8

Synthesis of Ruthenium Complex ((R,R)—BL-N-06-BF$_4$) (Ruthenium Complex of Formula (3))

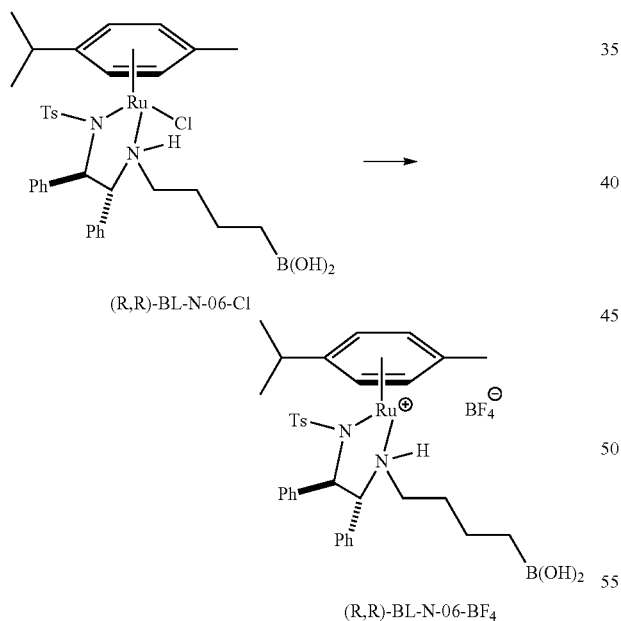

In 15 mL of methanol, 0.235 g (0.3192 mmol) of the ruthenium complex (R,R)—BL-N-06-Cl obtained in Example 7 and 0.075 g (0.38 mmol) of AgBF$_4$ were stirred for 1 hour, and the precipitated salt was filtered through Celite. Then, the filtrate was concentrated with an evaporator, and dried under reduced pressure. Thus, 0.19 g of (R,R)—BL-N-06-BF$_4$, which was a ruthenium complex of the present invention, was obtained (yield: 75.7%).

HRMS (ESI) calcd for C$_{35}$H$_{44}$BN$_2$O$_4$RuS [M-BF$_4$]$^+$ 701.2158. found 701.2133.

Example 9

Synthesis of ((1S,2S)-2-(4-Methylphenylsulfonamido)-1,2-diphenylethylamino)methylphosphonic Acid (Diamine Compound of Formula (1))

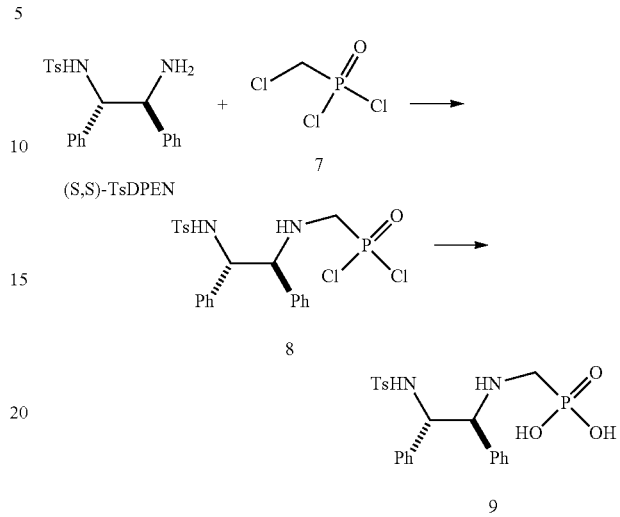

In 35 mL of toluene, 5.0 g (13.64 mmol) of (S,S)-TsDPEN, 2.28 g (1.39 mL, 13.64 mmol) of chloromethylphosphonic acid dichloride (compound 7), and 3.53 g (4.75 mL, 27.3 mmol) of DIPEA were dissolved, and a reaction was conducted in an oil bath of 130° C. for 10 hours. After that, the reaction liquid was cooled to normal temperature, and 15 mL of water was added thereto, followed by stirring for 30 minutes. The aqueous layer was separated from the reaction liquid, and extraction from the separated aqueous layer with 10 mL of ethyl acetate was conducted twice. To the combined organic layers, 50 mL of water and 3.0 g of NaOH were added, followed by stirring. After phase separation, extraction from the organic layer with 10 mL of a 0.1 M aqueous NaOH solution was conducted twice, and the aqueous layers were combined. The pH was adjusted to approximately 6 by adding concentrated hydrochloric acid. The aqueous layer was directly concentrated with an evaporator to approximately 20 mL. After the precipitated crystals were filtered, the crystals were washed with 20 mL of water, and dried under reduced pressure. Thus, 6.1 g of compound 9, which was a diamine compound of formula (1) according to the present invention, was obtained (yield: 54.2%).

$^1$H-NMR (CD$_3$OD, 300 MHz): δ 7.42-7.20 (d, 2H), 7.20-6.85 (m, 12H), 4.35 (d, 2H), 3.00-2.80 (m, 2H), 2.31 (s, 3H).

Example 10

Synthesis of Ruthenium Complex ((S,S)—PL-N-01-Cl) (Ruthenium Complex of Formula (2))

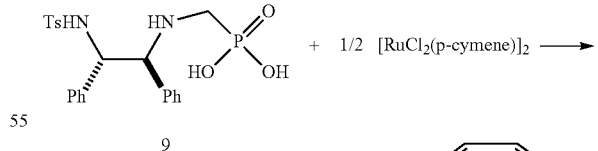

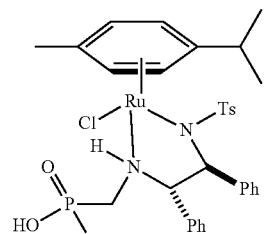

(S,S)-PL-N-01-Cl

In 5 mL of methanol, 0.25 g (0.543 mmol) of diamine compound 9 obtained in Example 9, 0.166 g (0.271 mmol) of [RuCl$_2$(p-cymene)]$_2$, and 0.1645 g (0.227 mL, 1.628 mmol) of triethylamine were dissolved, and a reaction was conducted at 50° C. for 2 hours. After that, the solvent was recovered from the reaction liquid, followed by purification by silica gel column chromatography (EtOAc/MeOH=2/1 (volume ratio)). Thus, 0.26 g of (S,S)—PL-N-01-Cl, which was a ruthenium complex of the present invention, was obtained (yield: 65.70).

HRMS (ESI) calcd for C$_{32}$H$_{38}$N$_2$O$_5$PRuS [M-Cl]$^+$ 695.1283. found 695.1297.

Example 11

Synthesis of Ruthenium Complex ((S,S)—PL-N-01-BF$_4$) (Ruthenium Complex of Formula (3))

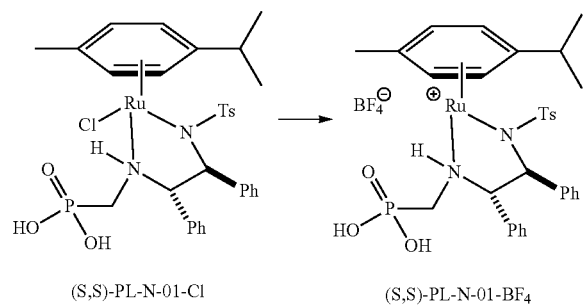

(S,S)-PL-N-01-Cl        (S,S)-PL-N-01-BF$_4$

A solution obtained by dissolving 0.444 g (0.6025 mmol) of the ruthenium complex (S,S)—PL-N-01-Cl obtained in Example 10 in 5 mL of dichloromethane was mixed with a solution obtained by dissolving 0.141 g (0.723 mmol) of AgBF$_4$ in 5 mL of methanol. The mixture was stirred for 1 hour, and the precipitated salt was filtered through Celite. Then, the filtrate was concentrated with an evaporator, and dried under reduced pressure. Thus, 0.42 g of (S,S)—PL-N-01-BF$_4$, which was a ruthenium complex of the present invention, was obtained (yield: 89.4%).

HRMS (ESI) calcd for C$_{32}$H$_{38}$N$_2$O$_5$PRuS [M-BF$_4$]$^+$ 695.1283. found 695.1265.

Example 12

Hydrogenation Reaction of 2-Methylquinoline with (S,S)—BL-N-09-BF$_4$ (Asymmetric Reduction Reaction of the Present Invention)

In a 100 mL autoclave, 3.8 mg (0.005 mmol, S/C=500) of (S,S)—BL-N-09-BF$_4$ obtained in Example 4 as a catalyst, 0.358 g (0.34 mL, 2.5 mmol) of 2-methylquinoline, and 2 mL of HFIP were placed, and a reaction was conducted under a hydrogen pressure of 5 MPa at 40° C. for 18 hours. The conversion and the optical purity determined by GC analysis were 95.8% conv. (conversion) and 95.3% ee (optical purity), respectively.

Comparative Example 1

Hydrogenation Reaction of 2-Methylquinoline with RuBF$_4$((R,R)-Tsdpen)(p-cymene)

A reaction conducted in the same manner as in Example 12, except that 3.4 mg (0.005 mmol) of RuBF$_4$((R,R)-Tsdpen)(p-cymene) was used as a catalyst. The conversion and the optical purity determined by GC analysis were 46.0% conv. (conversion) and 96.9% ee (optical purity), respectively.

The results of Example 12 and Comparative Example 1 are summarized below.

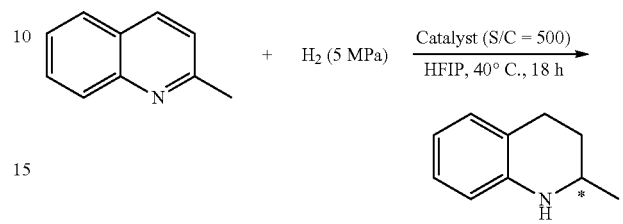

TABLE 1

| Catalyst | | Conversion (% conv) | Optical Purity (% ee) |
|---|---|---|---|
| Example 12 | (S,S)-BL-N-09-BF$_4$ | 95.8 | 95.3 |
| Comparative Example 1 | RuBF$_4$((R,R)-Tsdpen) (p-cymene) | 46.0 | 96.9 |

As described above, the BL-N-09-BF$_4$ complex of the present invention was compared with the conventionally used RuBF$_4$(Tsdpen)(p-cymene) complex in the same catalytic amount. It can be understood that the complex of the present invention achieved almost the same optical purity, and had a high activity with a value of the conversion being 2 or more times higher than that achieved by the conventionally used complex.

Example 13

Hydrogenation Reaction of 2-Methylquinoxaline with (S,S)—BL-N-09-BF$_4$ (Asymmetric Reduction Reaction of the Present Invention)

In a 100 mL autoclave, 7.5 mg (0.01 mmol, S/C=100) of (S,S)—BL-N-09-BF$_4$ obtained in Example 4 as a catalyst, 0.144 g (0.13 mL, 1.0 mmol) of 2-methylquinoxaline, and 1 mL of HFIP were placed, and a reaction was conducted under a hydrogen pressure of 5 MPa at 40° C. for 18 hours. The conversion and the optical purity determined by GC analysis were 97.9% conv. (conversion) and 94.1% ee (optical purity), respectively.

Comparative Example 2

Hydrogenation Reaction of 2-Methylquinoxaline with RuBF$_4$((R,R)-Tsdpen)(p-cymene)

A reaction was conducted in the same manner as in Example 13, except that 6.9 mg (0.01 mmol, S/C=100) of RuBF$_4$((R,R)-Tsdpen)(p-cymene) was used as a catalyst. The conversion and the optical purity determined by GC analysis were 42.2% conv. (conversion) and 92.8% ee (optical purity), respectively.

The results of Example 13 and Comparative Example 2 are summarized below.

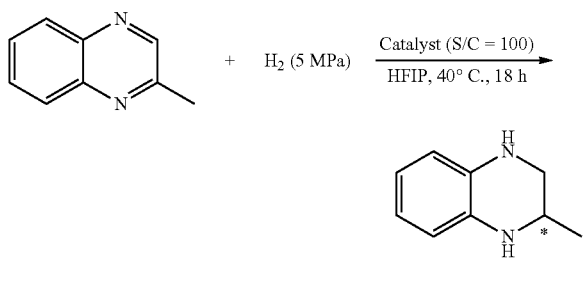

TABLE 2

| Catalyst | | Conversion (% conv) | Optical Purity (% ee) |
|---|---|---|---|
| Example 13 | (S,S)-BL-N-09-BF$_4$ | 97.9 | 94.1 |
| Comparative Example 2 | RuBF$_4$((R,R)-Tsdpen) (p-cymene) | 42.2 | 92.8 |

As described above, the BL-N-09-BF$_4$ complex of the present invention was compared with the conventionally used RuBF$_4$(Tsdpen)(p-cymene) complex under the condition using an HFIP solvent in the same catalytic amount. It can be understood that the complex of the present invention achieved a slightly improved optical purity, and had a high activity with a value of the conversion being 2 or more times higher than that achieved by the conventionally used complex.

Example 14

Hydrogenation Reaction of 2-Methylquinoxaline with (S,S)—PL-N-01-BF$_4$ (Asymmetric Reduction Reaction of the Present Invention)

In a 100 mL autoclave, 7.8 mg (0.01 mmol, S/C=100) of (S,S)—PL-N-01-BF$_4$ obtained in Example 11 as a catalyst, 0.144 g (0.13 mL, 1.0 mmol) of 2-methylquinoxaline, and 1 mL of toluene were placed, and a reaction was conducted under a hydrogen pressure of 5 MPa at 40° C. for 18 hours. The conversion and the optical purity determined by GC analysis were 89.1% conv. (conversion) and 77.1% ee (optical purity), respectively.

Comparative Example 3

Hydrogenation Reaction of 2-Methylquinoxaline with RuBF$_4$((R,R)-Tsdpen)(p-cymene)

A reaction was conducted in the same manner as in Example 14, except that 6.9 mg (0.01 mmol, S/C=100) of RuBF$_4$((R,R)-Tsdpen)(p-cymene) was used as a catalyst. The conversion and the optical purity determined by GC analysis were 96.5% conv. (conversion) and 70.7% ee (optical purity), respectively.

The results of Example 14 and Comparative Example 3 are summarized below.

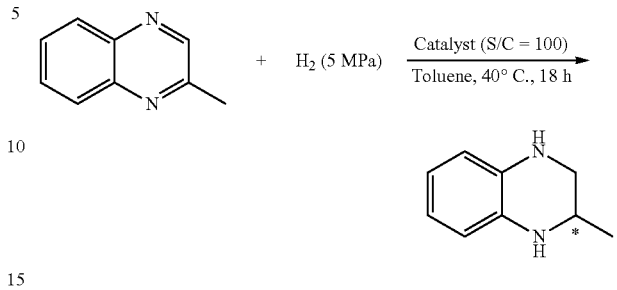

TABLE 3

| Catalyst | | Conversion (% conv) | Optical Purity (% ee) |
|---|---|---|---|
| Example 14 | (S,S)-PL-N-01-BF$_4$ | 89.1 | 77.1 |
| Comparative Example 3 | RuBF$_4$((R,R)-Tsdpen) (p-cymene) | 96.5 | 70.7 |

As described above, the PL-N-01-BF$_4$ complex of the present invention was compared with the conventionally used RuBF$_4$(Tsdpen)(p-cymene) complex under a condition using toluene as a solvent in the same catalytic amount. It can be understood that the complex of the present invention has a high selectivity, because the optical purity was greatly improved, although the conversion was slightly lowered.

Example 15

Hydrogenation Reaction of 2,3,3-Trimethylindolenine with (S,S)—BL-N-09-BF$_4$ (Asymmetric Reduction Reaction of the Present Invention)

In a 100 mL autoclave, 7.5 mg (0.01 mmol, S/C=100) of (S,S)—BL-N-09-BF$_4$ obtained in Example 4 as a catalyst, 0.159 g (0.16 mL, 1.0 mmol) of 2,3,3-trimethylindolenine, and 1 mL of HFIP were placed, and a reaction was conducted under a hydrogen pressure of 5 MPa at 40° C. for 18 hours. The conversion and the optical purity determined by GC analysis were 100% conv. (conversion) and 96.1% ee (optical purity), respectively.

Comparative Example 4

Hydrogenation Reaction of 2,3,3-Trimethylindolenine with RuBF$_4$((R,R)-Tsdpen)(p-cymene)

A reaction was conducted in the same manner as in Example 15, except that 6.9 mg (0.01 mmol, S/C=100) of RuBF$_4$((R,R)-Tsdpen)(p-cymene) was used as a catalyst. The conversion and the optical purity determined by GC analysis were 100% conv. (conversion) and 90.3% ee (optical purity), respectively.

The results of Example 15 and Comparative Example 4 are summarized below.

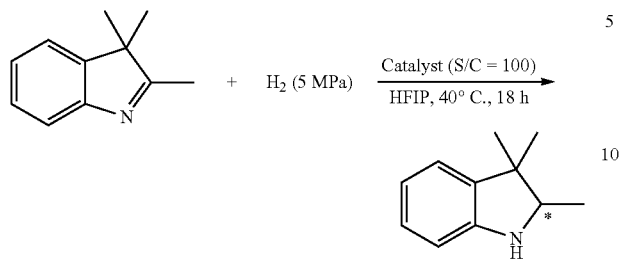

TABLE 4

| Catalyst | | Conversion (% conv) | Optical Purity (% ee) |
|---|---|---|---|
| Example 15 | (S,S)-BL-N-09-BF₄ | 100 | 96.1 |
| Comparative Example 4 | RuBF₄((R,R)-Tsdpen) (p-cymene) | 100 | 90.3 |

As described above, the BL-N-09-BF₄ complex of the present invention was compared with the conventionally used RuBF₄(Tsdpen)(p-cymene) complex in the same catalytic amount (S/C=100). The reaction was completed in each of the cases. It can be understood that the complex of the present invention has a high selectivity, because the optical purity was greatly improved in the case where the complex of the present invention was used.

Example 16

Synthesis of N-((1S,2S)-1,2-Diphenyl-2-(2-(4,4,5,5-tetramethyl-1,3,2-dioxaborolan-2-yl)benzylamino)ethyl)-4-methylbenzene sulfonamide (Raw Material for Synthesizing Diamine Compound of Formula (1))

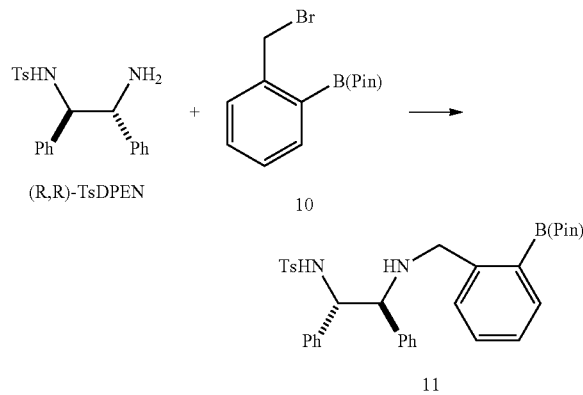

In 15 mL of toluene, 2.55 g (6.97 mmol) of (R,R)-TsDPEN, 2.07 g (6.97 mmol) of 2-bromomethylphenylboronic acid pinacol ester (compound 10), and 1.74 g (2.34 mL, 13.46 mmol) of DIPEA were dissolved, and a reaction was conducted in an oil bath of 120° C. under reflux for 3 hours. The reaction liquid was cooled with ice, and the precipitated salt was filtered. Then, the solvent was removed with an evaporator, and the concentrate was purified by silica gel column chromatography (EtOAc/hexane=5/1 (volume ratio)→2/1). Thus, 1.79 g of compound 11 was obtained (yield: 44.0%).

¹H-NMR (CD₃OD, 300 MHz): δ 7.82-6.55 (m, 18H), 4.90 (d, 1H), 4.70 (d, 1H), 3.50-3.38 (m, 2H), 2.35 (s, 3H), 1.10 (s, 12H).

Example 17

Synthesis of 2-(((1S,2S)-2-(4-Methylphenylsulfonamido)-1,2-diphenylethyl amino)methyl)phenylboronic Acid (Diamine Compound of Formula (1))

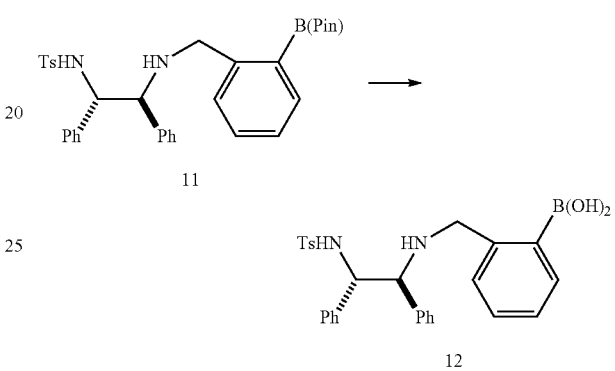

In a mixture solvent of 8 mL of THF and 2 mL of water, 1.79 g (3.072 mmol) of compound 11 obtained in Example 16 and 1.97 g (9.216 mmol) of NaIO₄ were reacted with each other at normal temperature for 2 hours. After that, 2 mL of a 2 N aqueous HCl solution was added to the reaction liquid, and a reaction was conducted at 30° C. for 12 hours. To this reaction liquid, 100 mL of ethyl acetate and 50 mL of water were added, followed by stirring. Then, the aqueous layer was removed by phase separation. The organic layer was dried over MgSO₄, and then the MgSO₄ was removed by filtration. The obtained filtrate was concentrated with an evaporator to about 3 mL. To the liquid concentrate, 80 mL of diethyl ether was added, and the precipitated crystals were filtered. Thus, 1.46 g of compound 12, which was a diamine compound of formula (1) according to the present invention, was obtained (yield: 95.0%).

¹H-NMR (CD₃OD, 300 MHz): δ 7.50-6.60 (m, 18H), 4.80-4.50 (m, 1H), 4.40-4.00 (m, 2H), 3.50-3.40 (m, 1H), 2.30 (s, 3H).

Example 18

Synthesis of Ruthenium Complex ((S,S)—BL-N-10-Cl) (Ruthenium Complex of Formula (2))

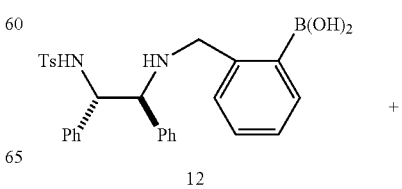

+

1/2 [RuCl₂(p-cymene)]₂ ⟶

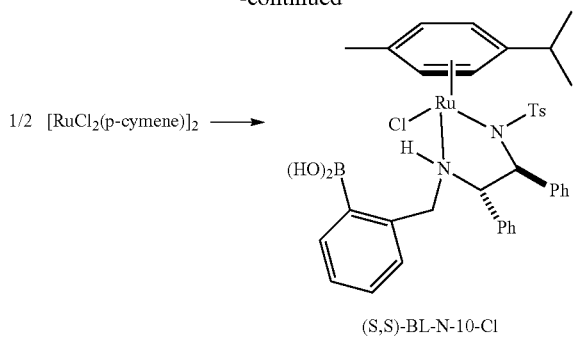

(S,S)-BL-N-10-Cl

In 14 mL of 2-propanol, 0.70 g (1.399 mmol) of diamine compound 12 obtained in Example 17, 0.428 g (0.70 mmol) of [RuCl₂(p-cymene)]₂, and 0.283 g (0.39 mL, 2.798 mmol) of triethylamine were dissolved, and a reaction was conducted at 60° C. for 30 minutes. After that, the solvent was recovered from the reaction liquid, and purification by silica gel column chromatography (chloroform/MeOH=20/1 (volume ratio)) was conducted. Thus, 0.95 g of (S,S)—BL-N-10-Cl, which was a ruthenium complex of the present invention, was obtained (yield: 88.2%).

HRMS (ESI) calcd for $C_{38}H_{42}BN_2O_4RuS$ [M-Cl]⁺ 35.2002. found 735.2022.

Example 19

Synthesis of Ruthenium Complex ((S,S)—BL-N-10-BF₄) (Ruthenium Complex of Formula (3))

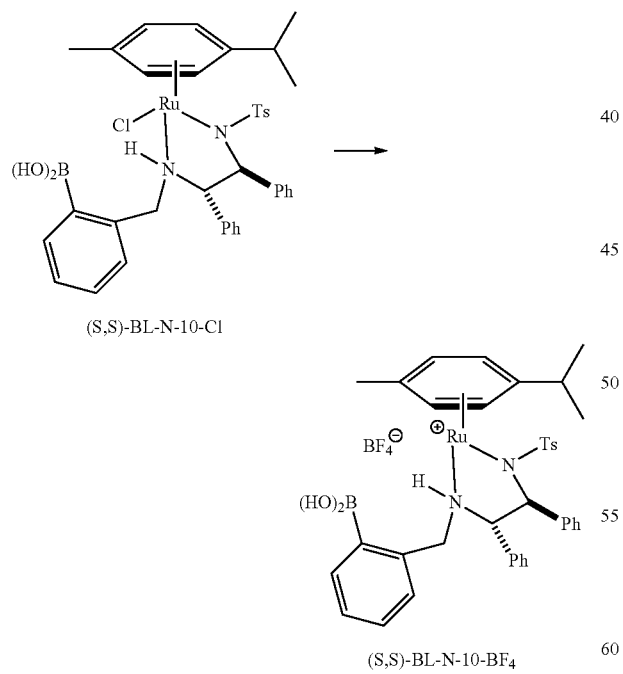

A solution obtained by dissolving 0.90 g (1.168 mmol) of the ruthenium complex (S,S)—BL-N-10-Cl obtained in Example 18 in 10 mL of dichloromethane and a solution obtained by dissolving 0.273 g (1.40 mmol) of AgBF₄ in 10 mL of methanol were mixed with each other, and the mixture was stirred for 2 hours. The precipitated salt was filtered through Celite. Then, the filtrate was concentrated with an evaporator, and dried under reduced pressure. Thus, 0.80 g of (S,S)—BL-N-10-BF₄, which was a ruthenium complex of the present invention, was obtained (yield: 83.4%).

HRMS (ESI) calcd for $C_{38}H_{42}BN_2O_4RuS$ [M-BF₄]⁺ 735.2002. found 735.2015.

Example 20

Synthesis of Iridium Complex ((S,S)—BL-N-09-Cl—IrCP*) (Iridium Complex of Formula (4))

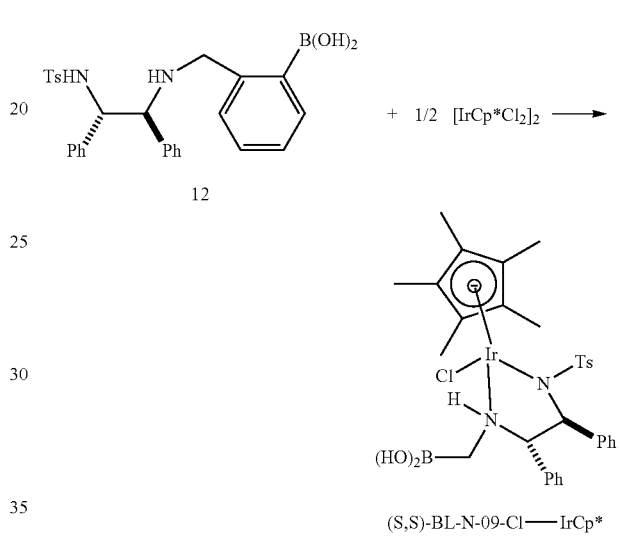

In 20 mL of dichloromethane, 0.50 g (1.178 mmol) of diamine compound 12 obtained in Example 17, 0.47 g (0.589 mmol) of [IrCp*Cl₂]₂, and 0.23 g (0.32 mL, 2.357 mmol) of triethylamine were dissolved, and a reaction was conducted at room temperature for 3 hours. After that, 10 mL of water was added to the reaction liquid, followed by stirring. The aqueous layer was separated, the organic layer was dried by using MgSO₄, and the solvent was removed from the obtained organic layer. Thus, 0.85 g of (S,S)—BL-N-09-Cl—IrCp*, which was an iridium complex of the present invention, was obtained (yield: 91.8%).

HRMS (ESI) calcd for $C_{32}H_{39}BIrN_2O_4S$ [M-Cl]⁺ 751.2353. found 751.2330.

Example 21

Synthesis of Iridium Complex ((R,R)—BL-N-06-Cl—IrCp*) (Iridium Complex of Formula (4))

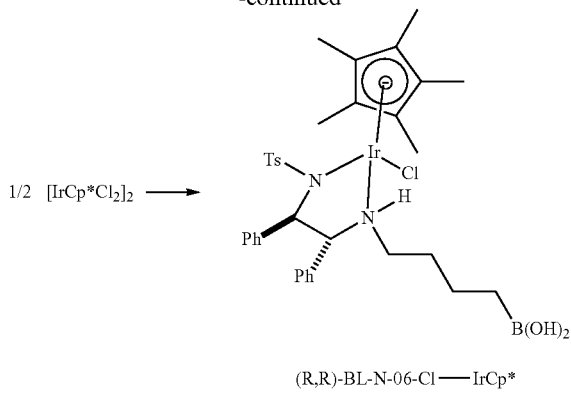

(R,R)-BL-N-06-Cl—IrCp*

In 15 mL of dichloromethane, 0.30 g (0.643 mmol) of diamine compound 6 obtained in Example 6, 0.428 g (0.322 mmol) of [IrCp*Cl₂]₂, and 0.13 g (0.18 mL, 1.286 mmol) of triethylamine were dissolved, and a reaction was conducted at room temperature for 30 minutes. After that, the solvent was recovered from the reaction liquid, and purification was conducted by silica gel column chromatography (ethyl acetate: 100%). Thus, 0.31 g of (R,R)—BL-N-06-Cl—IrCp*, which was an iridium complex of the present invention, was obtained (yield: 58.2%).

HRMS (ESI) calcd for $C_{35}H_{45}BIrN_2O_4S$ [M-Cl]⁺ 793.2822. found 793.2820.

Example 22

Synthesis of Iridium Complex ((R,R)—BL-N-06-BF₄—IrCP*) (Iridium Complex of Formula (5))

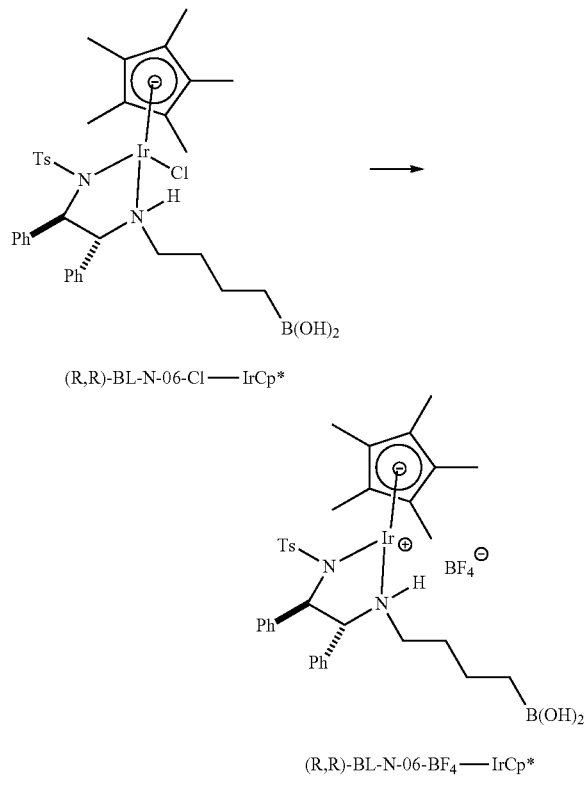

(R,R)-BL-N-06-Cl—IrCp*

(R,R)-BL-N-06-BF₄—IrCp*

In 20 mL of methanol, 0.31 g (0.374 mmol) of the iridium complex (R,R)—BL-N-06-Cl—IrCp* obtained in Example 21 and 0.081 g (0.41 mmol) of AgBF₄ were stirred for 1.5 hours, and the precipitated salt was filtered through Celite. Then, the filtrate was concentrated with an evaporator, and dried under reduced pressure. Thus, 0.28 g of (R,R)—BL-N-06-BF₄—IrCP*, which was an iridium complex of the present invention, was obtained (yield: 85.1%).

HRMS (ESI) calcd for $C_{35}H_{45}BIrN_2O_4S$ [M-BF₄]⁺ 793.2822. found 793.2803.

The present invention provides a ruthenium complex, iridium complex, and rhodium complex having a novel diamine compound as a ligand.

The ruthenium complex, iridium complex, and rhodium complex of the present invention are useful as asymmetric reduction catalysts which have very high catalytic activity and excellent stereoselectivity, and which achieve high enantiomeric excess.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. A diamine compound represented by the following formula (1):

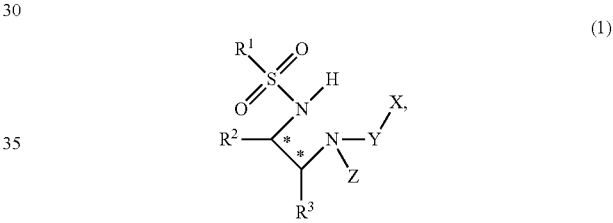

wherein
each * represents an asymmetric carbon atom,
$R^1$ represents a group selected from alkyl groups having 1 to 10 carbon atoms, halogenated alkyl groups having 1 to 10 carbon atoms, and aryl groups having 6 to 30 carbon atoms, the aryl groups optionally having one or more substituents selected from alkyl groups having 1 to 10 carbon atoms, halogenated alkyl groups having 1 to 10 carbon atoms, and halogen atoms,
$R^2$ and $R^3$ each independently represent a group selected from alkyl groups having 1 to 10 carbon atoms, phenyl groups, and cycloalkyl groups having 3 to 8 carbon atoms, the phenyl groups optionally having one or more substituents selected from alkyl groups having 1 to 10 carbon atoms, alkoxy groups having 1 to 10 carbon atoms, and halogen atoms, and each hydrogen atom of the cycloalkyl groups being optionally replaced by an alkyl group having 1 to 10 carbon atoms, or $R^2$ and $R^3$ together form a cycloalkane,
Y represents an alkylene group selected from optionally branched alkylene groups having 1 to 10 carbon atoms, and alkylene groups containing a benzene ring as a skeleton, the benzene ring optionally having one or more substituents selected from alkyl groups having 1 to 10 carbon atoms, alkoxy groups having 1 to 10 carbon atoms, and halogen atoms,
X represents a Brønsted acid selected from a boric acid group (—B(OH)₂), a carboxyl group (—COOH), a phosphoric acid group (—P(=O)(OH)$_2$), and phosphoric acid monoester groups (—P(=O)(OH)(OR$^{21}$)), where R$^{21}$ represents an alkyl group having 1 to 5 carbon atoms, and Z represents a hydrogen atom or a deuterium atom.

2. A ruthenium complex represented by the following formula (2) or (3), or an iridium complex or rhodium complex represented by the following formula (4) or (5):

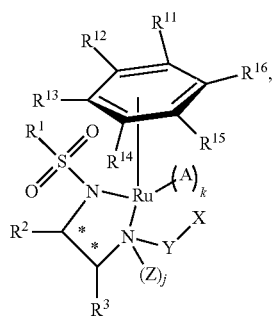
(2)

wherein
each * represents an asymmetric carbon atom,
R$^1$, R$^2$, R$^3$, X, Y, and Z are as defined in claim 1,
R$^{11}$, R$^{12}$, R$^{13}$, R$^{14}$, R$^{15}$, and R$^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and C(=O)—OR$^{22}$, where R$^{22}$ represents an alkyl group having 1 to 10 carbon atoms, a heteroaryl group having 4 to 10 carbon atoms, or an aryl group having 6 to 10 carbon atoms,
A represents a group selected from a trifluoromethanesulfonyloxy group, a p-toluenesulfonyloxy group, a methanesulfonyloxy group, a benzenesulfonyloxy group, a hydrogen atom, and halogen atoms, and
j and k each represent 0 or 1, but j+k is not 1;

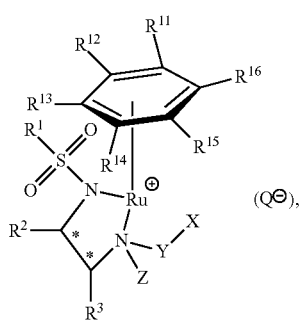
(3)

wherein
each * represents an asymmetric carbon atom,
R$^1$, R$^2$, R$^3$, X, Y, and Z are as defined in claim 1,
R$^{11}$, R$^{12}$, R$^{13}$, R$^{14}$, R$^{15}$, and R$^{16}$ are as defined above, and
Q$^-$ represents a counter anion;

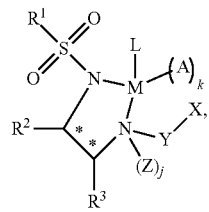
(4)

wherein
each * represents an asymmetric carbon atom,
R$^1$, R$^2$, R$^3$, X, Y, and Z are as defined in claim 1,
A represents a group selected from a trifluoromethanesulfonyloxy group, a p-toluenesulfonyloxy group, a methanesulfonyloxy group, a benzenesulfonyloxy group, a hydrogen atom, and halogen atoms,
M represents iridium or rhodium,
L represents a cyclopentadienyl or pentamethylcyclopentadienyl ligand, and
j and k each represent 0 or 1, but j+k is not 1;

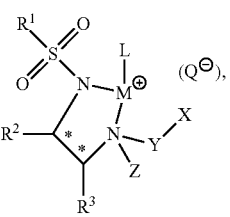
(5)

wherein
each * represents an asymmetric carbon atom,
R$^1$, R$^2$, R$^3$, X, Y, and Z are as defined in claim 1,
M and L are as defined above, and
Q$^-$ represents a counter anion.

3. A method for producing an optically active amine or an optically active compound, comprising:
reducing an imino group of an imine compound or an unsaturated bond of a heterocyclic compound in the presence of the complex according to claim 2 and a hydrogen donor.

4. The production method according to claim 3, wherein the hydrogen donor is hydrogen.

5. The production method according to claim 3, wherein the hydrogen donor is selected from the group consisting of a formic acid, an alkali metal formate, and an alcohol having a hydrogen atom on a carbon atom at an α-position of a carbon atom substituted with a hydroxyl group.

6. A catalyst for asymmetric reduction, comprising the complex according to claim 2.

7. A method for asymmetric reduction of an imine compound or a heterocyclic compound comprising: reducing an imino group of the imine compound or an unsaturated bond of the heterocyclic compound in the presence of a catalyst comprising the complex according to claim 2 and a hydrogen donor.

* * * * *